US012797390B2

(12) United States Patent
Burdine et al.

(10) Patent No.: US 12,797,390 B2
(45) Date of Patent: Nov. 17, 2026

(54) INHIBITORS OF DNA PK AND USES THEREOF

(71) Applicants: BioVentures, LLC, Little Rock, AR (US); Arkansas Children's Research institute, Little Rock, AR (US)

(72) Inventors: Lyle Burdine, Little Rock, AR (US); Marie Burdine, Little Rock, AR (US); Ara Kim Wiese, Little Rock, AR (US)

(73) Assignees: BioVentures, LLC; Arkansas Children's Research institute

( * ) Notice: Subject to any disclaimer, the term of this patent is extended or adjusted under 35 U.S.C. 154(b) by 80 days.

(21) Appl. No.: 18/583,207

(22) Filed: Feb. 21, 2024

(65) Prior Publication Data

US 2024/0245696 A1 Jul. 25, 2024

Related U.S. Application Data

(63) Continuation of application No. 16/499,773, filed as application No. PCT/US2018/025430 on Mar. 30, 2018, now abandoned.

(60) Provisional application No. 62/479,945, filed on Mar. 31, 2017.

(51) Int. Cl.

| | |
|---|---|
| ***A61K 31/5377*** | (2006.01) |
| ***A61K 31/7088*** | (2006.01) |
| ***A61P 37/06*** | (2006.01) |
| *A61K 9/00* | (2006.01) |

(52) U.S. Cl.

CPC .......... *A61K 31/5377* (2013.01); *A61P 37/06* (2018.01); *A61K 9/0014* (2013.01); *A61K 9/0019* (2013.01); *A61K 9/0053* (2013.01); *A61K 31/7088* (2013.01)

(58) Field of Classification Search

CPC .... A61K 31/47; A61K 31/498; A61K 31/505; A61K 31/5377; A61K 31/7088

See application file for complete search history.

(56) References Cited

U.S. PATENT DOCUMENTS

| | | | |
|---|---|---|---|
| 4,241,046 | A | 12/1980 | Papahadjopoulos et al. |
| 4,394,448 | A | 7/1983 | Szoka, Jr. et al. |
| 4,529,561 | A | 7/1985 | Hunt et al. |
| 4,755,388 | A | 7/1988 | Heath et al. |
| 4,828,837 | A | 5/1989 | Uster et al. |
| 4,925,661 | A | 5/1990 | Huang |
| 4,954,345 | A | 9/1990 | Muller |
| 4,957,735 | A | 9/1990 | Huang |
| 5,043,164 | A | 8/1991 | Huang et al. |
| 5,064,655 | A | 11/1991 | Uster et al. |
| 5,077,211 | A | 12/1991 | Yarosh |
| 5,264,618 | A | 11/1993 | Felgner et al. |
| 7,179,912 | B2 | 2/2007 | Halbrook et al. |
| 7,981,893 | B2 | 7/2011 | Mortensen et al. |
| 8,242,115 | B2 | 8/2012 | Halbrook et al. |
| 8,404,681 | B2 | 3/2013 | Halbrook et al. |
| 9,000,153 | B2 | 4/2015 | Fuchss et al. |
| 9,376,448 | B2 | 6/2016 | Charifson et al. |
| 9,592,232 | B2 | 3/2017 | Charifson et al. |
| 2007/0167441 | A1 | 7/2007 | Halbrook et al. |
| 2008/0090782 | A1 | 4/2008 | Halbrook et al. |
| 2009/0082327 | A1 * | 3/2009 | Czarnik ............... C07D 477/20 514/210.13 |
| 2012/0039867 | A1 | 2/2012 | Weyand et al. |
| 2013/0109687 | A1 | 5/2013 | Nabel et al. |
| 2013/0245027 | A1 | 9/2013 | Xu et al. |
| 2013/0281431 | A1 | 10/2013 | Charifson et al. |
| 2013/0289271 | A1 | 10/2013 | Perrin-Ninkovic et al. |
| 2014/0199415 | A1 | 7/2014 | Westermarck et al. |
| 2015/0258127 | A1 * | 9/2015 | Terzi .................... A61K 31/635 514/262.1 |

FOREIGN PATENT DOCUMENTS

| | | | | |
|---|---|---|---|---|
| WO | 03/024949 | A1 | 3/2003 | |
| WO | 2004/085418 | A2 | 10/2004 | |
| WO | 2009/008991 | A2 | 1/2009 | |
| WO | 2011/137428 | A1 | 11/2011 | |
| WO | 2015/188119 | A1 | 12/2015 | |
| WO | WO-2016138300 | A1 * | 9/2016 | ......... A61K 31/7088 |
| WO | 2016/210046 | A1 | 12/2016 | |
| WO | 2018/183868 | A1 | 10/2018 | |

OTHER PUBLICATIONS

Vilchez (Transplant International vol. 30 pp. 1061-1074 published 2017) (Year: 2017).*
Kong (Biol. Pharm. Bull. Vol. 32 pp. 297-300. Published 2009) (Year: 2009).*
Shin (Immunotherapy vol. 6 pp. 419-430 published 2014). (Year: 2014).*
Joosten (Kidney International vol. 69 pp. 1-13 published 2005). (Year: 2005).*
Chase (Massachusetts General Hospital Press Release Feb. 7, 2025) (Year: 2025).*
Alt, F. et al., "Ordered rearrangement of immunoglobulin heavy chain variable region segments," EMBO J., 1984, pp. 1209-1219, vol. 3, No. 6.
Bird, R. et al., "Single-Chain Antigen-Binding Proteins," Sci., Oct. 1988, pp. 423-426, vol. 242, No. 4877.
Born, W. et al., "Rearrangement of T-cell receptor beta-chain genes during T-cell development," PNAS, May 1985, pp. 2925-2929, vol. 82.
Boyman, O. et al., "The role of interleukin-2 during homeostasis and activation of the immune system," Nat. Rev. Immunol., Mar. 2012, pp. 180-190, vol. 12.

(Continued)

*Primary Examiner* — George W Kosturko
(74) *Attorney, Agent, or Firm* — Polsinelli PC

(57) ABSTRACT

The present disclosure relates to compositions and methods for improving the transplantation outcome and/or reducing immune response in a subject. The compositions comprise a DNA-PK inhibitor.

17 Claims, 14 Drawing Sheets
(8 of 14 Drawing Sheet(s) Filed in Color)
Specification includes a Sequence Listing.

(56) References Cited

OTHER PUBLICATIONS

Burdine, L. et al., "Proteomic Identification of DNA-PK Involvement within the RET Signaling Pathway," PloS ONE, Jun. 2015, pp. 1-14, vol. 10, No. 6, e0127943.

Burma, S. et al., "Role of DNA-PK in the cellular response to DNA double-strand breaks," DNA Repair, 2004, pp. 909-918, vol. 3, Nos. 8-9.

Chen, B. et al., "Cell Cycle Dependence of DNA-dependent Protein Kinase Phosphorylation in Response to DNA Double Strand Breaks," J_ Biol. Chem., Apr. 2005, pp. 14709-14715, vol. 280, No. 15.

Chen, B. et al., "Ataxia Telangiectasia Mutated (ATM) Is Essential for DNA-PKcs Phosphorylations at the Thr-2609 Cluster upon DNA Double Strand Break," J_ Biol. Chem., Mar. 2007, pp. 6582-6587, vol. 282, No. 9.

Choi, S-Y. et al., "Phosphorylation and ubiquitination-dependent degradation of CABIN1 releases p53 for transactivation upon genotoxic stress," Nucleic Acids Res., 2013, pp. 2180-2190, vol. 41, No. 4.

Davis, A. et al., "Dynamics of the PI3K-like protein kinase members ATM and DNA-PKcs at DNA double strand breaks," Cell Cycle, Jul. 2010, pp. 2529-2536, vol. 9, No. 13.

Davis, A. et al., "DNA double strand break repair via non-homologous end-joining," Transl. Cancer Res., 2013, pp. 130-143, vol. 2, No. 3.

Dennis, P. et al., "Target of rapamycin (TOR): balancing the opposing forces of protein synthesis and degradation," Curr. Opin. Genet. Dev., 1999, pp. 49-54, vol. 9.

Disanto, J_ et al., "Interleukin-2 (IL-2) receptor gamma chain mutations in X-linked severe combined Immunodeficiency disease result in the loss of high-affinity IL-2 receptor binding," Eur. J. Immunol., Feb. 1994, pp. 175-479, vol. 24, No. 2.

Dragoi, A-M. et al., "DNA-PKcs, but not TLR9, is required for activation of Akt by CpG-DNA," EMBO J., 2005, pp. 779-789, vol. 24.

Esau, C. et al., "Deletion of Calcineurin and Myocyte Enhancer Factor 2 (MEF2) Binding Domain of Cabin1 Results in Enhanced Cytokine Gene Expression in T Cells," J. Exp. Med., Nov. 2001, pp. 1449-1459, vol. 194, No. 10.

Gao, Y. et al., "A Targeted DNA-PKcs-Null Mutation Reveals DNA-PK-Independent Functions for KU in V(D)J Recombination," Immunity, Sep. 1998, pp. 367-376, vol. 9.

Golding, S. et al., "Pro-survival AKT and ERK signaling from EGFR and mutant EGFRvlll enhances DNA doublestrand break repair in human glioma cells," Cancer Biol. Ther., Apr. 2009, pp. 730-738, vol. 8, No. 8.

Gupta, S. et al., "The leucine rich region of DNA-PKcs contributes to its innate DNA affinity," Nucleic Acids Res., 2005, pp. 6972-6981, vol. 33, No. 22.

Hein, A. et al., "Radiation-induced signaling pathways that promote cancer cell survival (Review)," International J. Oncol., 2014, pp. 1813-1819, vol. 45.

Hogan, P. et al., "Transcriptional regulation by calcium, calcineurin, and NFAT," Genes Dev., 2003, pp. 2205-2232, vol. 17.

Holliger, P. et al., "'Diabodies': Small bivalent and bispecific antibody fragments," PNAS, Jul. 1993, pp. 6444-6448, vol. 90.

Huston, J. et al., "Protein engineering of antibody binding sites: Recovery of specific activity in an anti-digoxin singlechain Fv analogue produced in *Escherichia coli*," PNAS, Aug. 1988, pp. 5879-5883, vol. 85.

International Search Report and Written Opinion dated Jun. 20, 2018 from related Patent Application No. PCT/US2018/025430; 10 pgs.

Jang, H. et al., "Cabin1 restrains p53 activity on chromatin," Nat. Struct. Mol. Biol., Sep. 2009, pp. 910-915, vol. 16, No. 9.

Jhappan, C. et al., "DNA-PKcs: a T-cell tumour suppressor encoded at the mouse scid locus," Nat. Genet., Dec. 1997, pp. 483-486, vol. 17.

Leahy, J. et al., "Identification of a highly potent and selective DNA-dependent protein kinase (DNA-PK) inhibitor (NU7441) by screening of chromenone libraries," Bioorg. Med. Chem. Lett., Dec. 2004, pp. 6083-6087, vol. 14, No. 24.

Li, J. et al., "Regulation of CHK2 by DNA-dependent Protein Kinase," J. Biol. Chem., Mar. 2005, pp. 12041-12050, vol. 280, No. 12.

Liao, W. et al., "IL-2 Family Cytokines: New Insights into the Complex Roles of IL-2 as a Broad Regulator of T helper Cell Differentiation," NIH Public Access Author Manuscript, Oct. 1, 2012, pp. 1-12, published in final edited form as: Curr. Opin. Immunol., Oct. 2011, pp. 598-604, vol. 23, No. 5.

Malek, T. et al., "Interleukin-2 Receptor Signaling: At the Interface between Tolerance and Immunity," Immunity, Aug. 2010, pp. 153-165, vol. 33.

Minjgee, M. et al., "K-RAS(V12) Induces Autocrine Production of EGFR Ligands and Mediates Radioresistance Through EGFR-Dependent AKT Signaling and Activation of DNA-PKCS," Int. J. Radial. Oncol. Biol. Phys., Dec. 2011, pp. 1506-1514, vol. 81, No. 5.

Ossbourn, J. et al., "Directed selection of MIP-1alpha neutralizing CCR5 antibodies from a phage display human antibody library," Nat. Biotechnol., 1998, pp. 778-781, vol. 16.

Poljak, R., "Production and structure of diabodies," Structure, Dec. 1994, pp. 1121-1123, vol. 2.

Sun, L. et al., "Cabin 1, A Negative Regulator for Calcineurin Signaling in T Lymphocytes," Immunity, Jun. 1998, pp. 703-711, vol. 8.

Taccioli, G. et al., "Targeted Disruption of the Catalytic Subunit of the DNA-PK Gene in Mice Confers Severe Combined Immunodeficiency and Radiosensitivity," Immunity, Sep. 1998, pp. 355-366, vol. 9.

Ting, N. et al., "DNA-dependent Protein Kinase Interacts with Antigen Receptor Response Element Binding Proteins NF90 and NF45," J. Biol. Chem., Jan. 1998, pp. 2136-2145, vol. 273, No. 4.

Toulany, M. et al., "Akt Promotes Post-Irradiation Survival of Human Tumor Cells through Initiation, Progression, and Termination of DNA-PKcs-Dependent DNA Double Strand Break Repair," Mol. Cancer Res., 2012, pp. 945-957, vol. 10, No. 7.

Tsai, A. et al., "A Multikinase and DNA-PK Inhibitor Combination Immunomodulates Melanomas, Suppresses Tumor Progression, and Enhances Immunotherapies," Cancer Immunol. Res., Sep. 2017, pp. 790-803, vol. 5, No. 9.

Van Der Burg, M. et al., "DNA-PKcs deficiency in human: long predicted, finally found," Curr. Opin. Allergy Clin. Immunol., Dec. 2009, pp. 503-509, vol. 9, No. 6.

Van Triest, B. et al., "A phase Ia/Ib trial of the DNA-dependent protein kinase inhibitor (DNA-PKi) M3814 in Combination with radiotherapy in patients with advanced solid tumors," J. Clin. Oncol., 2017, vol. 35, Suppl. 15, e14048, 1 pg.

Ward, E. et al., "Binding activities of a repertoire of single immunoglobulin variable domains secreted from *Escherichia coli*," Nature, Oct. 1989, pp. 544-546, vol. 341.

Wiese, A. et al., "DNA-PKcs controls calcineurin mediated IL-2 production in T lymphocytes," PLoS ONE, Jul. 2017, pp. 1-12, vol. 12, No. 7, e0181608.

Wong, R. et al., "A Role of DNA-PK for the Metabolic Gene Regulation in Response to Insulin," Cell, Mar. 2009, pp. 1056-1072, vol. 136.

Acosta et al (International Journal of Immunopathology and Pharmacology vol. 27 pp. 53-67 published 2014) (Year: 2014).

Ghonim, M.A. et al., (J. Allergy Clin. Immunology vol. 135 pp. 425-440. Published 2015). (Year: 2015).

Non-Final Office Action for U.S. Appl. No. 16/499,773 dated Apr. 8, 2021 (59 Pages).

Final Office Action for U.S. Appl. No. 16/499,773 dated Oct. 12, 2021 (34 Pages).

Non-Final Office Action for U.S. Appl. No. 16/499,773 dated Jun. 14, 2022 (192 Pages).

Final Office Action for U.S. Appl. No. 16/499,773 dated Dec. 28, 2022 (282 Pages).

Non-Final Office Action for U.S. Appl. No. 16/499,773 dated Sep. 21, 2023 (76 Pages).

(56) References Cited

OTHER PUBLICATIONS

Notice of Restriction Requirement for U.S. Appl. No. 16/499,773 dated Nov. 2, 2020 (15 Pages).

* cited by examiner

INHIBITORS OF DNA PK AND USES THEREOF

CROSS REFERENCE TO RELATED APPLICATIONS

This application is a Continuation of U.S. application Ser. No. 16/499,773, filed Sep. 30, 2019 which claims the benefit of International application number PCT/US2018/025430, filed Mar. 30, 2018, which claims the benefit of U.S. Provisional Application No. 62/479,945, filed Mar. 31, 2017, the disclosures of which are hereby incorporated by reference in their entirety.

GOVERNMENTAL RIGHTS

This invention was made with government support under grant P20 GM121293 awarded by National Institutes of Health. The government has certain rights in the invention.

REFERENCE TO SEQUENCE LISTING

The present application contains a Sequence Listing which has been submitted electronically in .XML format and is hereby incorporated herein by reference in its entirety. Said computer readable file, was created on Feb. 20, 2024 is named 2017_24_052592_USDIV1.xml and is 17.7 kilobytes in size.

FIELD OF THE INVENTION

The present disclosure relates to compositions and methods for improving the transplantation outcome and/or reducing immune response in a subject.

BACKGROUND OF THE INVENTION

DNA-dependent protein kinase (DNA-PK) is a 460 kDa polypeptide member of the PI3k family. DNA-PK is believed to serve as a recruiting and scaffolding protein for DNA ligase.

IL-2 is a T cell-derived cytokine that influences a multitude of key elements in the immune response including the proliferation and differentiation of B and T lymphocytes. Expression of IL-2 is initiated upon calcineurin activation. Calcineurin is a calcium and calmodulin-dependent protein serine/threonine phosphatase that upon activation, dephosphorylates Nuclear Factor of Activated T-cells (NFAT) allowing it to translocate to the nucleus and upregulate expression of target genes (including IL-2). IL-2 then binds to its receptor IL-2R, expressed on the surface of lymphocytes, to induce signaling that impacts both arms of the immune response, humoral and cellular immunity.

Allograft rejection is an immune response, involving activated T-lymphocytes. Currently used immunosuppressive protocols designed to inhibit rejection involve the administration of drugs such as azathioprine, cyclosporine, and corticosteroids, all of which cause toxic side-effects to non-lymphoid tissues. T-lymphocytes orchestrate both the initiation and propagation of immune responses largely through the secretion of interleukin-2 (IL-2). IL-2 is primarily involved in the regulation of T-lymphocyte proliferation but also activates natural killer (NK), B- and lymphokine-activated killer (LAK) cells. Inappropriate responses of T-lymphocytes are associated with a range of immune diseases, including allergies and autoimmune diseases.

Therefore, what is needed, is a method to reduce or suppress IL-2 production to reduce the immune response.

SUMMARY OF THE INVENTION

One aspect of the present disclosure is directed to a method of improving the transplantation outcome in a subject receiving an organ transplant. The method comprises administering to the subject a therapeutically effective amount of a composition comprising a DNA-PK inhibitor, wherein the DNA-PK inhibitor improves the transplantation outcome.

Another aspect of the present disclosure is directed to a method of reducing immune response in a subject in need thereof. The method comprises administering to the subject a therapeutically effective amount of a composition comprising a DNA-PK inhibitor, wherein the DNA-PK inhibitor reduces an immune response.

An additional aspect of the present disclosure is directed to a method of reducing an immune response in a subject receiving an organ or tissue transplant. The method comprises administering to the subject a therapeutically effective amount of a composition comprising a DNA-PK inhibitor, wherein the DNA-PK inhibitor improves the transplantation outcome.

BRIEF DESCRIPTION OF THE FIGURES

The patent or application file contains at least one drawing executed in color. Copies of this patent or patent application publication with color drawing(s) will be provided by the Office upon request and payment of the necessary fee.

(FIG. 1A) Jurkat cells were treated with the DNA-PKcs inhibitor NU7441 at varying concentrations for 48 hours and no significant reduction in viability was detected. (FIG. 1B) Jurkat cells were stimulated with PMA (50 ng/ml)+PHA (1 μg/mL), treated with NU7441, and analyzed for IL-2 production 24 hours later. NU7441 treatment significantly blocked IL-2 secretion. (FIG. 1C) IL-2 production stimulated by activation of Jurkat cells with anti-CD28/CD3 dynabeads at a 1:1 ratio for 24 hours was inhibited by NU7441 treatment. (FIG. 1D) Treatment of Jurkat cells with shRNA reduced DNA-PKcs expression at 2.5 and 5 μg as seen by western blot analysis. Loss of DNA-PKcs expression significantly reduced IL-2 production. (FIG. 1E) NU7441 significantly reduce IL-2 production following activation with PHA+PMA in PBMCs.  $p<0.002$ * $p<0.001$ error bars=s.d.

(FIG. 2A) Western blot analysis of Jurkat cell lysates showed activation of T cells with PMA+PHA induced phosphorylation of DNA-PKcs at site s2056 (pDNA-PK) and dephosphorylated NFAT at s237 (pNFAT). Treatment with NU7441 inhibited the dephosphorylation of NFAT at site s237 which is critical for its translocation to the nucleus. GAPDH was used as a loading control. (FIG. 2B) Immunocytochemistry analysis of Jurkat cells treated with NU7441. The inhibitor (2.5 M) blocked translocation of NFAT to the nucleus following activation with PMA+PHA. Nuclei were stained with Dapi. 40× images are shown.

(FIG. 3A) Jurkat cells were activated with PMA+PHA, treated with the DNA-PKcs inhibitor NU7441 (2.5 UM) and monitored for calcineurin phosphatase activity. Inhibition caused a significant reduction in calcineurin activity. (FIG. 3B) Level of $Ca^{2+}$ in Jurkat cell lysates following activation with PMA+PHA was monitored. $Ca^{2+}$ levels were not affected by the addition of the NU7441 inhibitor. (FIG. 3C) Western blot and Elisa analysis of active phosphorylated mTOR in activated Jurkat cells indicated that inhibition of DNA-PKcs does not alter mTOR activation. *** p<0.001 error bars=s.d.

(FIG. 4A) Western blot analysis of Jurkat lysates following activation with PMA+PHA and NU7441 treatment. Activation increased phosphorylation of DNA-PKcs and CHK2. DNA-PKcs inhibition reduced CHK2 phosphorylation and elevated Cabin1 expression. GAPDH was used as a loading control. (FIG. 4B) Schematic depicting the signaling pathway in T cells used by DNA-PKcs to regulate IL-2 production. DNA-PKcs phosphorylates CHK2 which in turns phosphorylates Cabin1 targeting it for destruction. This alleviates calcineurin inhibition causing an increase in translocation of NFAT and IL-2 production. CaN, calcineurin.

(FIG. 6C) decreased rejection with DNA-PK(cs) inhibitor.

(FIG. 7A) depicts PD1-expression in presence of NU7441 vs. FK506. (FIG. 7B) depicts IL-2 expression in presence of NU7441 vs. FK506.

(FIG. 8A): T-Bet, (FIG. 8B): Lymphotoxin.

(FIG. 9A): Batf3, (FIG. 9B): RoRγt, (FIG. 9C): IL22, (FIG. 9D): TGFBeta, (FIG. 9E): IL17.

DETAILED DESCRIPTION OF THE INVENTION

Figure 1A:
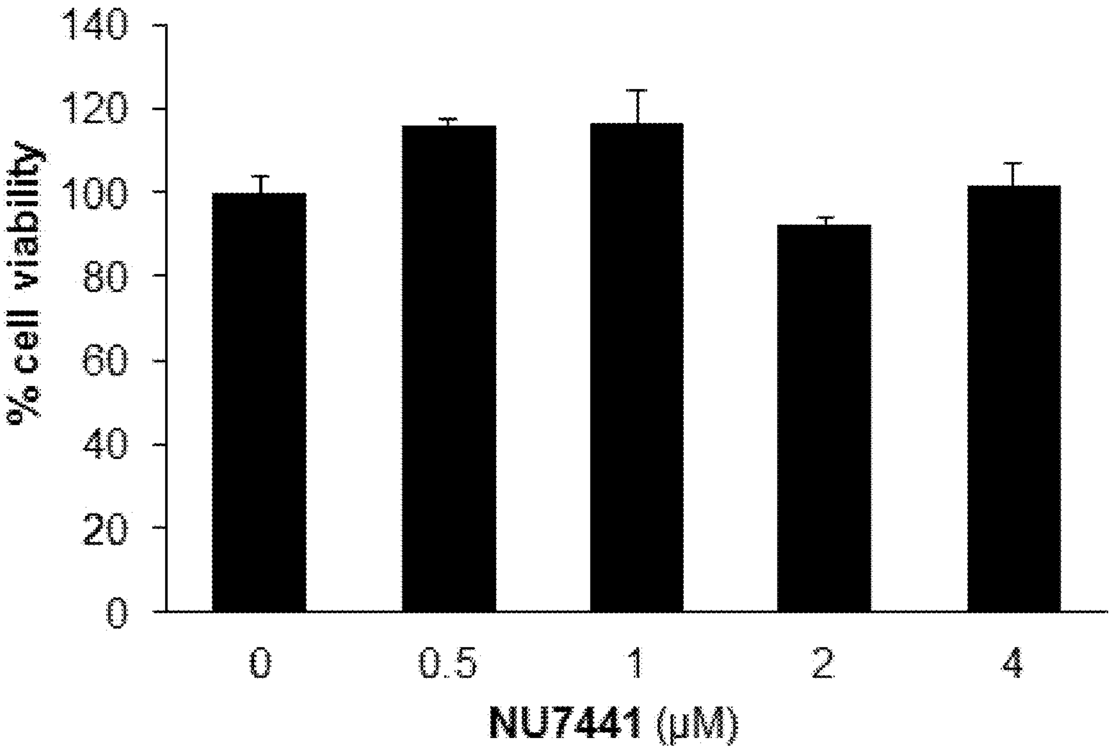
FIG. 1A, FIG. 1B, FIG. 1C, FIG. 1D, and FIG. 1E depict inhibition of DNA-PKcs in T cells and PBMCs blocks IL-2 production.

Provided herein are compositions and methods for improving the transplantation outcome and reducing immune response in a subject.

Additional aspects of the invention are described below.

(I) Compositions

One aspect of the present disclosure encompasses a composition comprising at least one DNA-PK inhibitor. In some embodiments, the DNA-PK may be inhibited by a nucleotide, an antibody, or a small molecule inhibitor.

A composition of the present disclosure may optionally comprise one or more additional drug(s) or therapeutically active agent(s) in addition to the DNA-PK inhibitor. A composition of the invention may further comprise a pharmaceutically acceptable excipient, carrier, or diluent. Further, a composition of the invention may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents, or antioxidants.

Other aspects of the invention are described in further detail below.

(a) Nucleotide and Antibody Inhibitors

In general, the DNA-PK inhibitor may comprise a nucleotide inhibitor or an antibody inhibitor. In some embodiments, the DNA-PK inhibitor may comprise a nucleotide inhibitor. In other embodiments, DNA-PK inhibitor may comprise an antibody inhibitor.

(i) Nucleotide Inhibitor

In general, a nucleotide DNA-PK inhibitor may be an RNA sequence. The RNA sequence may be a short-hairpin RNA (shRNA). The shRNA may be used to reduce expression of DNA-PK. In an embodiment, the sequence of the shRNA may comprise GCGACATATTATGGAAGAATT (SEQ ID NO: 6); CCACCCAACAACAATATGATT (SEQ ID NO: 7); or GCCATACAAATGTGGAATTAA (SEQ ID NO: 8).

Without being bound by theory, it is believed that the shRNA bind DNA-PK nucleotides which encode the LRR (leucine rich region) motif between amino acid resides 1503-1602 of DNA-PK and corresponds to a DNA binding domain. (see, for instance, Nucleic Acids Res. 2005 Dec. 9; 33(22):6972-81.)

(ii) Antibody Inhibitor

In general, an antibody inhibitor may be an anti-DNA-PK antibody.

Examples of anti-DNA-PK antibodies may include, without limit, ab174576, ab18192, ab32566, ab124918, ab18356, ab230, ab4194, ab4194, ab168854, ab70250, ab44815, ab69527, ab174575, ab133516, ab195537, ab133441, ab97611, and ab218129. These antibodies are commercially available. In other embodiments, an antibody inhibitor may be a single chain antibody, chimeric antibody, or humanized antibody that comprises the sequence responsible for the binding specificity of ab174576, ab18192, ab32566, ab124918, ab18356, ab230, ab4194, ab4194, ab168854, ab70250, ab44815, ab69527, ab174575, ab133516, ab195537, ab133441, ab97611, or ab218129.

(b) Small Molecules

In general, a DNA-PK inhibitor may comprise a small molecule inhibitor. The small molecule inhibitors detailed herein include compounds that inhibit DNA-PK. Compounds known to inhibit DNA-PK are known in the art. See for example, U.S. Pat. Nos. 9,376,448; 9,592,232; 8,242,115; 7,179,912; US 2013/0109687; WO 2011/137428; U.S. Pat. No. 8,404,681; and US 2008/0090782; the disclosures of which are hereby incorporated by reference. The DNA-PK inhibitors described herein inhibit an activity of a DNA-PK polypeptide by a percentage of inhibition. Further, the DNA-PK inhibitors inhibit the DNA-PK polypeptide by 50%, by 60%, by 70%, or by 80%. The percentage of inhibition may be determined by an in vitro biochemical assay, an in vitro cell-based assay, or in an in vivo assay. Additionally assays are known to those of skill in the art.

In an embodiment, the small molecule inhibitor may be (VX-984)

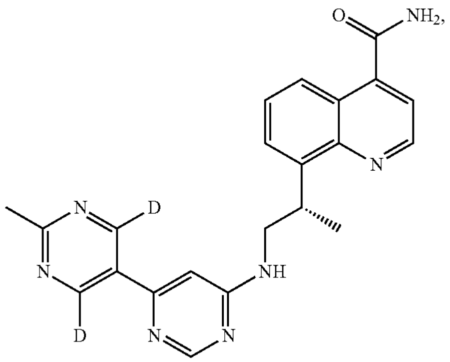

(CC-115)

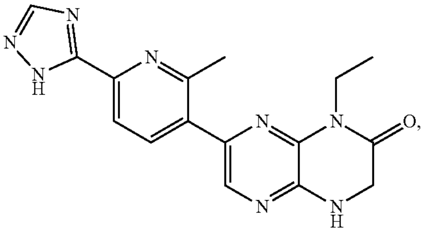

(NU7441)

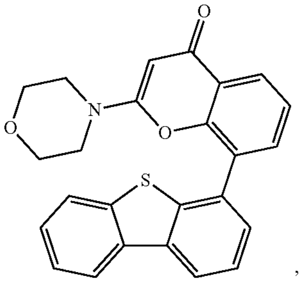

, (NU-7026)

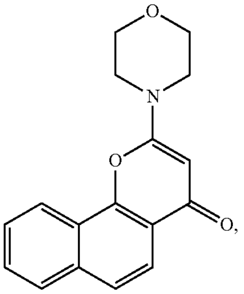

or an analog thereof.

In other embodiments, the small molecule inhibitor may be selected from the group consisting of (VX-984)

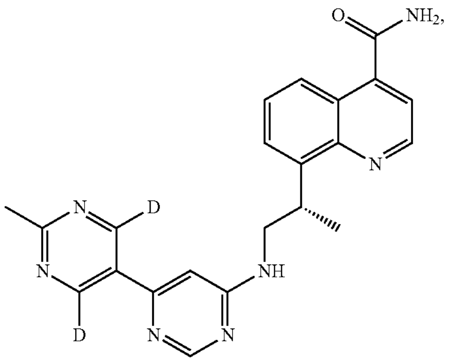

(CC-115)

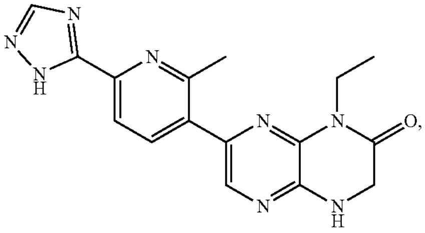

and (NU7441)

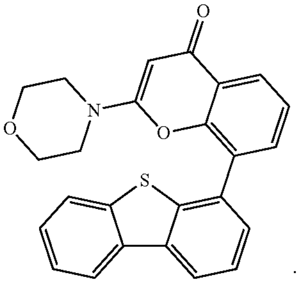

.

(II) Pharmaceutical Compositions

Another aspect of the present disclosure provides pharmaceutical compositions. The pharmaceutical compositions comprise at least one DNA-PK inhibitor and at least one pharmaceutical acceptable excipient.

(a) Composition

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

(i) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Binder

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

(iii) Filler

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(iv) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(v) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vi) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isomorphous silicate, and microcrystalline cellulose.

(viii) Excipient

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Taste-Masking Agent

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xi) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

(b) Administration (i) Dosage Forms

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. ($18^{th}$ ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising at least one DNA-PK inhibitor is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of at least one DNA-PK inhibitor in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, at least one DNA-PK inhibitor may be selectively delivered to a cell by encapsulation in a liposome that fuses with the targeted cell's membrane.

Liposomes may be comprised of a variety of different types of phospholipids having varying hydrocarbon chain lengths. Phospholipids generally comprise two fatty acids linked through glycerol phosphate to one of a variety of polar groups. Suitable phospholipids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tetradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchlorate, 3,3'-deheptyloxacarbocyanine iodide, 1,1'-dedodecyl- 3,3,3',3'-tetramethylindocarbocyanine perchlorate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchlorate.

Liposomes may optionally comprise sphingolipids, in which sphingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying at least one DNA-PK inhibitor may be prepared by any known method of preparing liposomes for drug delivery, such as, for example, detailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied. These parameters include, but are not limited to, temperature, pH, concentration of the DNA-PK inhibitor, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. At least one DNA-PK inhibitor may be encapsulated in a microemulsion by any method generally known in the art.

In yet another embodiment, at least one DNA-PK inhibitor may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

(ii) Dosage

Dosages of the pharmaceutical compositions can vary between wide limits, depending upon the disease or disorder to be treated, the age of the subject, and the condition of the subject to be treated. In an embodiment, the amount of the DNA-PK inhibitor in the pharmaceutical composition is an amount to effectively inhibit DNA-PK.

(iii) Subject

A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas, and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

(III) Methods

In an aspect, the present disclosure provides methods of reducing IL-2 secretion in T cells. The method comprises contacting a T cell with a composition comprising a DNA-PK inhibitor of the present invention. Suitable DNA-PK inhibitors are disclosed herein, for instance those described in Section I. In some embodiments, the DNA-PK inhibitor in the present invention inhibits production of IL-2 by activated T cells compared to activated T-cells which have not been contacted with a DNA-PK inhibitor. IL-2 expression and/or secretion may be measured according to standard methods known in the art, including those described in the Examples.

Contacting the T cell with a DNA-PK inhibitor composition may occur in vitro, in vivo, or ex vivo. For example, in one aspect, the invention provides contacting a cell culture comprising T-cells with a composition comprising a DNA-PK inhibitor of the invention. In another aspect, the invention provides a method of contacting T-cells in a subject by administering a composition comprising a DNA-PK inhibitor of the invention.

An additional aspect is a method for treating a disease or disorder caused by IL-2 production or acceleration of IL-2 receptor expression. In this aspect, a DNA-PK inhibitor is administered to a subject for prophylaxis or treatment of a disease or disorder caused by IL-2 production or acceleration of IL-2 receptor expression. The IL-2 related diseases in the present invention are diseases caused by IL-2 production or acceleration of IL-2 receptor expression. By way of non-limiting example, IL-2 related diseases may include AIDS, skin diseases (psoriasis, atopic dermatitis, urticaria), internal diseases (lupus nephritis), ophthalmic diseases (allergic conjunctivitis, sty, chalazion, spring catarrh, uveitis, cancer), autoimmune diseases (polymyositis, Hashimoto's disease, Behcet's disease, ankylosing spondylitis, systemic sclerosis, Sjogren's syndrome, pollenosis, scleroderma), gastrointestinal diseases, inflammatory diseases (gout, psoriatic arthritis, rheumatoid arthritis), central nervous system diseases (multiple sclerosis), respiratory diseases (asthma, chronic obstructive pulmonary disease), fibromyalgia, myasthenia gravis, sarcoidosis, nasal inflammation, and nasal catarrh.

Another aspect of the present disclosure encompasses a method of reducing an immune response in a subject. The method comprises administering to a subject an effective amount of a composition comprising a DNA-PK inhibitor. In some embodiments, the composition reduces an immune response in a subject by reducing cellular and/or humoral immunity in the subject. As used herein, the term "immune response" includes T cell mediated and/or B cell mediated immune responses. Non-limiting exemplary immune responses include T cell responses, e.g., cytokine production, and cellular cytotoxicity. In addition, the term immune response includes immune responses that are indirectly effected by T cell activation, e.g., antibody production (humoral responses) and activation of cytokine responsive cells, e.g., macrophages.

Reducing an immune response can be in the form of inhibiting or down-regulating an immune response already in progress or may involve preventing the induction of an immune response. For example, administration of a composition comprising a DNA-PK inhibitor to a subject may reduce cytokine production, cellular toxicity, antibody production or the activation of cytokine response cells compared to a control subject who has who has not been contacted with the composition. In another aspect, administration of a composition comprising a DNA-PK inhibitor may reduce cytokine production, cellular toxicity, antibody production or the activation of cytokine response cells compared to the same subject prior to administration of the DNA-PK inhibitor.

In yet another aspect, the present disclosure provides a method to improve the transplantation outcome in a subject receiving an organ or tissue transplant. In one aspect, the invention provides a method of reducing an immune response in a subject receiving an organ or tissue transplant.

In another aspect, the present invention provides reducing IL-2 secretion in T-cells of a subject receiving an organ or tissue transplant. The methods comprise administering to a subject receiving an organ or tissue transplant an effective amount of a composition comprising a DNA-PK inhibitor. In the various embodiments, administration may occur prior to transplantation, during transplantation or post-transplant.

In non-limiting examples, the transplant recipients may be recipients of kidney, liver, heart, heart-lung, bone-marrow, and cornea transplants. As used herein, the term "transplantation" refers to the process of taking a cell, tissue, or organ, called a "transplant" or "graft" from one individual and placing it or them into a (usually) different individual. The individual who provides the transplant is called the "donor" and the individual who received the transplant is called the "host" (or "recipient"). An organ, or graft, transplanted between two genetically different individuals of the same species is called an "allograft". A graft transplanted between individuals of different species is called a "xenograft". The organ transplant tissue itself is typically human in origin, but may also be from another species such as the rhesus monkey.

In accordance with the invention, in some embodiments, transplant recipients have improved transplantation outcomes including reduced transplant rejection in a subject. As used herein, "transplant rejection" is characterized by an acute or chronic diminution in the physiological function of a transplanted organ. Acute rejection typically occurs within the first year post transplantation and generally speaking is a consequence of cell-mediated immune response (e.g. T cells). Chronic rejection occurs several years following transplant resulting from antibody-mediated immune response (e.g. B cells). In some aspects, reduced transplant rejection in transplanted organ or tissue function is measured by biological factors specific to the organ transplanted. For example, for kidney transplant rejection assessment, decreased glomerular atrophy, reduced intimal thickening, reduced tubular atrophy, reduced interstitial fibrosis, reduced lymphocyte infiltration and reduced cortical scarring independently or taken together are indicators of reduced graft rejection. Similarly, for heart transplant reduced rejection assessment includes, reduced cardiac vessel disease post-transplant, and reduced graft intimal hyperplasia independently or taken together are indicators of reduced graft rejection. In non-limiting examples, reduced transplant rejection treatment is assessed in accordance with the present invention by one or more of the following organ-dependent parameters: decreased coronary graft intimal hyperplasia compared to grafted vessels in a subject not receiving a DNA-PK inhibitor; improved renal function as measured by serial serum creatinine levels; graft survival prolongation; hyalinization and cortical scarring in renal grafts; decreased lymphocytic infiltration, vasculitis, infarction, ischemia, thrombosis, intimal thickening, glomerular atrophy, glomerular sclerosis, tubular atrophy, hyalinization, interstitial fibrosis, cortical fibrosis, serum creatinine levels, intimal proliferation, hypertrophy, cardiac vessel disease post-transplant, graft intimal hyperplasia, luminal occlusion, or bronchitis obliterans. It is understood that the biological factors which can be measured as an indicator of reduced transplant rejection are specific to the organ transplanted and are understood by those skilled in the art.

In some embodiments, the methods of the invention provide a DNA-PK inhibitor of the present invention used in combination with one or more of a nonsteroidal anti-inflammatory agent, a steroidal anti-inflammatory agent, an immune suppressant, an antihistamine, an antirheumatic drug and a biological preparation such as infliximab, adalimumab, tocilizumab, etc. Non-limiting examples of suitable nonsteroidal anti-inflammatory agents may include indomethacin, ibuprofen, diclofenac, and aspirin. Non-limiting examples of suitable steroidal anti-inflammatory agents may include dexamethasone, betamethasone, prednisolone, and triamcinolone. Non-limiting examples of suitable immunosuppressants may include tacrolimus, cyclosporine, and sirolimus. Non-limiting examples of suitable antihistamines may include diphenhydramine, chlorpheniramine, triprolidine, promethazine, alimemazine, hydroxyzine, cyproheptadine, fexofenadine, olopatadine, epinastine, loratadine, cetirizine, bepotastine, and mequitazine. Non-limiting examples of suitable antirheumatic drugs may include bucillamine, salazosulfapyridine, and methotrexate.

(a) Administration

In certain aspects, a therapeutically effective amount of a composition of the invention may be administered to a subject. Administration is performed using standard effective techniques. In a preferred embodiment, a composition is administered orally, parenterally, or topically.

For therapeutic applications, a therapeutically effective amount of a composition of the invention is administered to a subject. A "therapeutically effective amount" is an amount of the therapeutic composition sufficient to produce a measurable response (e.g., decreased IL-2 expression, decreased organ transplant rejection, graft survival prolongation, and the like). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, age, disease or condition, the organ or tissue transplanted, the symptoms, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The timing of administration of the treatment is under stood to be relative to the timing of the transplantation or to disease itself and duration of treatment will be determined by the circumstances surrounding the case. For example, treatment may occur prior to transplantation or post-transplant. Treatment could begin in a hospital or clinic itself, or at a later time after discharge from the hospital or after being seen in an outpatient clinic.

Duration of treatment could range from a single dose administered on a one-time basis to a life-long course of therapeutic treatments. The duration of treatment can and will vary depending on the subject and the disease or disorder to be treated. For example, the duration of treatment may be for 1 day, 2 days, 3 days, 4 days, 5 days, 6 days, or 7 days. Or, the duration of treatment may be for 1 week, 2 weeks, 3 weeks, 4 weeks, 5 weeks or 6 weeks. Alternatively, the duration of treatment may be for 1 month, 2 months, 3 months, 4 months, 5 months, 6 months, 7 months, 8 months, 9 months, 10 months, 11 months, 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time. For example, duration of treatment may be 5 days, then no treatment for 9 days, then treatment for 5 days.

The frequency of dosing may be once, twice, three times or more daily or once, twice, three times or more per week or per month, or as needed as to effectively treat the symptoms or disease. In certain embodiments, the frequency of dosing may be once, twice or three times daily. For example, a dose may be administered every 24 hours, every 12 hours, or every 8 hours. In other embodiments, the frequency of dosing may be once, twice or three times weekly. For example, a dose may be administered every 2 days, every 3 days or every 4 days. In a different embodiment, the frequency of dosing may be one, twice, three or four times monthly. For example, a dose may be administered every 1 week, every 2 weeks, every 3 weeks or every 4 weeks.

(b) Subject

A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

The human subject may be of any age. In some embodiments, the human subject may be about 20, 25, 30, 40, 45, 50, 55, 60, 65, 70, 75, 80, 85, 90, 95 years of age or older. In some preferred embodiments, the human subject is 30 years of age or older. In other preferred embodiments, the human subject is 40 years of age or older. In other preferred embodiments, the human subject is 45 years of age or older. In yet other preferred embodiments, the human subject is 50 years of age or older. In still other preferred embodiments, the human subject is 55 years of age or older. In other preferred embodiments, the human subject is 60 years of age or older. In yet other preferred embodiments, the human subject is 65 years of age or older. In still other preferred embodiments, the human subject is 70 years of age or older. In other preferred embodiments, the human subject is 75 years of age or older. In still other preferred embodiments, the human subject is 80 years of age or older. In yet other preferred embodiments, the human subject is 85 years of age or older. In still other preferred embodiments, the human subject is 90 years of age or older.

Definitions

When introducing elements of the present disclosure or the preferred aspects(s) thereof, the articles "a," "an," "the," and "said" are intended to mean that there are one or more of the elements. The terms "comprising," "including," and "having" are intended to be inclusive and mean that there may be additional elements other than the listed elements.

The term "therapeutically effective amount" means the dose needed to effectively treat the physiological effects of graft rejection.

"IL-2" (Interleukin-2) is a cytokine produced mainly by activated T cells, and acts on the cells such as T cells, B cells, macrophages, etc. IL-2 promotes proliferation and activation of T cells, proliferation and acceleration of the antibody-producing ability of B cells, activation of monocytes and macrophages, proliferation and activation of natural killer cells (NK cell), and inducing action of lymphokine-activated killer cells, etc.

As used herein, the term "immune cell" includes cells that are of hematopoietic origin and that play a role in the immune response. Immune cells include lymphocytes, such as B cells and T cells; natural killer cells; myeloid cells, such as monocytes, macrophages, eosinophils, mast cells, basophils, and granulocytes.

As used herein, the term "T cell" includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., DNA-PK). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG molecules or other isotypes. VH and V1 can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g. Holliger, P., et al. (1993) Proc. Natl. Acad. Sci. USA 90:6444-6448; Poljak, R. J., et al. (1994) Structure 2:1121-1123).

As various changes could be made in the above-described materials and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: DNA-PKcs Controls Calcineurin Mediated IL-2 Production in T Lymphocytes Introduction The catalytic subunit of DNA-dependent protein kinase (DNA-PKcs) is a 460 kDa polypeptide member of the PI3k family. It was initially discovered to be a key component in non-homologous end-joining (NHEJ) which is the predominant pathway used to repair DNA double strand breaks in mammalian cells and is critical for V(D)J recombination [1, 2]. DNA-PKcs is believed to serve as a recruiting and scaffolding protein for DNA ligase [3]. Knock out of DNA-PKcs activity in mammals results in a Severe Combined Immunodeficiency (SCID) phenotype which is characterized by diminished levels of mature B and T cells [4-6]. This has been attributed to disruption of V(D)J recombination which is necessary for lymphocyte development and responsible for both antibody and T cell receptor diversity [7, 8]. Without being bound by theory, it is thought that this enzyme is involved in other aspects of the immune response including Interleukin-2 (IL-2) signaling since the disruption of the IL-2 pathway in IL-2 receptor mutants also results in a SCID phenotype [9]. Of note, DNA-PKcs has previously been associated with multiple receptor signaling pathways including EGF, RET, and the insulin signaling pathway and phosphorylates key molecules associated with cell growth, e.g., AKT [10-14].

Well described, IL-2 is a T cell-derived cytokine that influences a multitude of key elements in the immune response including the proliferation and differentiation of B and T lymphocytes [15]. Expression of IL-2 is initiated upon calcineurin activation. Calcineurin is a calcium and calmodulin-dependent protein serine/threonine phosphatase that upon activation, dephosphorylates Nuclear Factor of Activated T-cells (NFAT) allowing it to translocate to the nucleus and upregulate expression of target genes (including IL-2) [15-17]. IL-2 then binds to its receptor IL-2R, expressed on the surface of lymphocytes, to induce signaling that impacts both arms of the immune response, humoral and cellular immunity [18]. IL-2 is known to promote the expansion and maturation of B and T lymphocytes and regulates the differentiation of T cells into effector or regulatory T cells [15-17].

To evaluate the function of DNA-PKcs in this pathway, its activity was inhibited by either shRNA or the commercially available inhibitor NU7441 in Jurkat cells, a human T cell line, and the effect on IL-2 levels was analyzed. Inhibiting DNA-PKcs in activated Jurkat cells resulted in reduced calcineurin activity, loss of NFAT translocation to the nucleus and decreased IL-2 expression. It was showed that this effect was linked to the calcineurin inhibitor, Cabin1. Cabin1 directly binds to activated calcineurin and blocks its dephosphorylation of NFAT. Overexpressing full length Cabin1 or its N-terminal region in Jurkat cells has been shown to reduce IL-2 expression by inhibiting the calcineurin-NFAT pathway [19, 20]. Cabin1 was also identified to function in DNA damage by inhibiting activity of p53 [21]. Through these studies it was revealed that phosphorylation of Cabin1 by the checkpoint kinase CHK2 targets it for ubiquination and degradation [22]. Interestingly, phosphorylation by DNA-PKcs is known to regulate activity of CHK2. DNA-PKcs phosphorylates CHK2 at site Thr68 thereby activating the kinase [23]. It was showed that inhibiting DNA-PKcs in Jurkat cells resulted in a decrease in CHK2 phosphorylation causing an increase in Cabin1 expression. This novel pathway for regulation of IL-2 signaling indicates a much broader function for DNA-PKcs in the immune system than previously understood and further explains the development of a SCID phenotype in mice lacking DNA-PKcs activity.

Methods and Materials

Materials: PHA-L, PMA, X-treme GENE transfection reagent, and 0.1% poly-lysine solution were purchased from Sigma-Aldrich (St. Louis, MO). NU7441 was purchased from Selleckchem (Houston, TX). shRNA against DNA-PKcs was purchased from ORIGENE (Rockville, MD). Dynabeads Human T-Activator CD3/CD28 was purchased from Thermo Fisher Scientific (Waltham, MA).

Cell Culture: Human peripheral blood mononuclear cells (PBMC,) and Jurkat cells were purchased from ATCC (PCS-800-011, Manassas, VA). Cells were maintained at 37° C. in a humidified atmosphere composed of 5% $CO_2$. Jurkat cells were cultured in RPMI 1640 medium which was supplemented with 10% FCS and human PBMC was cultured in RPMI 1640 medium which was supplemented with 10% FCS and pen/strep. Both Jurkat cells and PBMC were stimulated with PHA (50 ng/mL) and PMA (1 μg/mL) for 24 hours prior to harvesting for IL-2 detection or 6 hours prior for western blot analysis. The NU7441 DNA-PKcs inhibitor was added at varying concentrations at the time of stimulation.

Knockdown of DNA-PKcs in Jurkat cells: Jurkat cells ($5\times10^5$ cells/well) were grown in 6-well plates. The cells were transfected with short-hairpin RNA (shRNA) plasmids generated by Origene. (2.5 μg of scramble (SEQ ID NO: 5) or 2.5 and 5 μg of specific to DNA-PKcs (SEQ ID NO: 1; SEQ ID NO: 2; SEQ ID NO: 3; and SEQ ID NO: 4)) using X-TREME GENE and incubated for 72 hours. Four shRNA plasmids were obtained from ORIGENE that target various regions of DNA-PKcs. The shRNA plasmid that provided the best knock down of DNA-PKcs expression was used for our experiments. The cells were subjected to Western blot analysis and IL-2 ELISA assay. shRNA plasmids against DNA-PKcs was purchased from ORIGENE (Rockville, MD).

Cell lysis and nuclear extract: Cells were washed with cold PBS twice and centrifuged at 5000 rpm for 5 minutes. For the nuclear extract, pellets were suspended with 800 μL of 10 mN HEPES lysis buffer (10 mM HEPES at pH 7.9, 10 mM KCl, 1 mM DTT, and 1× protease and phosphatase inhibitor) and incubated on ice for 15 minutes. 50 μL of NP-40 (10% in water) was added and the pellets were mixed for 10 seconds. Lysates were centrifuged for 5 minutes at 4° C. at 13,000 rpm. The supernatant solution which is containing the cytosolic fraction was discarded and the pellets were resuspended in 20 mM HEPES lysis buffer (20 mM HEPES at pH 7.9, 0.4 M NaCl, 1 mM DTT, and 1× protease, and phosphatase inhibitor) and incubated on ice for 15 minutes with intermittent mixing. Lysates were centrifuged for 10 minutes at 4° C. at 13,000 rpm. The supernatant containing nuclear extract was stored at −20° C. until they were used for the Western blot analysis. For total cell lysates, cell pellets were resuspended with 100 μL of RIPA buffer (150 mM NaCl, 1% Triton X-100, 0.1% SDS, and 50 mM Tris at pH 8.0) and incubated on ice for 10 minutes. The lysates were centrifuged for 10 minutes at 4° C. at 13,000 rpm and the supernatant solutions were stored at −20° C. until they were used for the Western blot analysis.

Western blot analysis: Nuclear extract lysates were separated on 3-8% Tris-Acetate gels (Invitrogen). Total cell lysates were separated on 4-20% Tris-Glycine gels (Bio-Rad). Gels were transferred onto PVDF membrane (Millipore) for 2 hours in the cold room at 100V. Immunoblotting was performed using following antibodies: pDNA-PKcs at S2056 (ab18192, Abcam), DNAPK (ab53701, Abcam), pNFAT2 at S237 (ab183023, Abcam), CABIN1 (12660S, Cell signaling), GAPDH (MAB374, Millipore), and Lamin B1 (ab16048, Abcam). HRP-conjugated secondary antibody anti-Rabbit and anti-Mouse (7074S and 7076S, Cell Signaling) was used.

Cell viability assay: Cell viability assay was performed using Promega CELLTITER 96 AQUEOUS One Solution Cell Proliferation Assay (Madison, WI) and following the manufacturer's protocol. Briefly, 100 μL of PBMC or Jurkat cells were plated in a 96-well plate and treated with various concentration of NU7441 for 48 hours. CELLTITER solution (20 μL/100 μL of cell suspension) was added to the cells and the plate was incubated for 3 hours at 37° C. and the absorbance at 490 nm was recorded using SynergyHTX (BioTek, Winooski, VT) plate reader.

Immunofluorescence of NFAT: Jurkat cells were plated in poly-lysine treated 35 mm dish with glass-bottom (BioTek) overnight. The cells were fixed with 4% formaldehyde and permeabilized with permeabilization solution (0.2% TRITON X-100+OVA solution (0.1 mg/mL), 0.01% sodium azide). NFAT was probed with anti-NFAT2 (ab2796, Abcam) in permeabilization solution overnight at 4° C., and then washed with PBS. Fluorescein (FITC)-conjugated AffiniPure Donkey Anti-Mouse IgG (715-095-151, Jackson ImmunoResearch) was applied to the cells for 1 hour at room temperature. The cells were washed with PBS and ProLong Antifade reagent with DAPI (Molecular Probes) was applied. All samples were analyzed on an Olympus Fluoview FV1000 laser confocal microscope. Images from all microscopy experiments were processed using the FV10-ASW 3.1 Viewer (Olympus).

Detection of secreted IL-2: Secreted IL-2 was detected by Human IL-2 ELISA Kit from Thermo Scientific (Waltham, MA). The manufacturer's protocol was followed. Prior to harvesting, cells were treated with PHA (50 ng/ml) and PMA (1 μg/mL) for 24 hours with or without the NU7441 inhibitor. Jurkat cells stimulated with the anti-CD28/CD3 dynabeads were done so according to the manufacturer's protocol at a 1:1 ratio for 24 hours prior to harvesting. After stimulation, supernatant samples of Jurkat cells or PBMCs (2 million cells/mL) were collected and diluted 10 times before the assay. IL-2 standards and samples (50 μL) and Biotinylated antibody reagents (50 μL) were added to each well and the plate was incubated for 3 hours at room temperature. The plate was washed 3 times and 100 μL of Streptavidin-HRP solution was added. After 30 minutes of incubation at room temperature, the plate was washed 3 times. TMB substrate (100 μL) was added and incubated for 30 minutes in the dark at room temperature. Stop solution was added and the absorbance of each well was read at 450 nm using the plate reader.

Detection of calcineurin and mTOR activities: Calcineurin phosphatase activity was detected by Calcineurin Cellular Activity Assay Kit from Millipore (Billerica, MA) and mTOR signaling was detected by Calcium Detection Kit from Abcam (Cambridge, MA). The manufacturer's protocols were followed. Briefly, Jurkat cells (2 million cells/mL) were lysed using lysis buffer. For calcineurin activity, the cell lysates were desalted by gel filtration to remove free phosphates before the assay and were subjected to calcineurin activity assay. The absorbance of each sample was read at 620 nm using the plate reader. For mTOR ELISA assay, the cell lysates were added to each well and antibody against phosphorylated mTOR at serine 2448 was used to detect the activity of mTOR signaling. The absorbance of each sample was read at 450 nm using the plate reader.

Measurements of calcium ions: Intracellular concentration of calcium ions was measured by Calcium Detection Assay Kit from Abcam (Cambridge, MA). The manufacturer's protocols were followed. Briefly, Jurkat cells (2 million cells/mL) were lysed using cold PBS with 0.1% NP-40. The cell lysates were diluted 10 times before use. After following the assay protocol, the absorbance of each sample was read at 575 nm using the plate reader.

Statistical analysis: Assays to monitor IL-2 levels, calcineurin and mTOR activities, and $Ca^{2+}$ ion levels were performed in both technical triplicate and biological triplicate. Standard student t-test were performed to compare group means. Means with p-value below 0.05 were considered statistically different.

Results

Figure 1B:
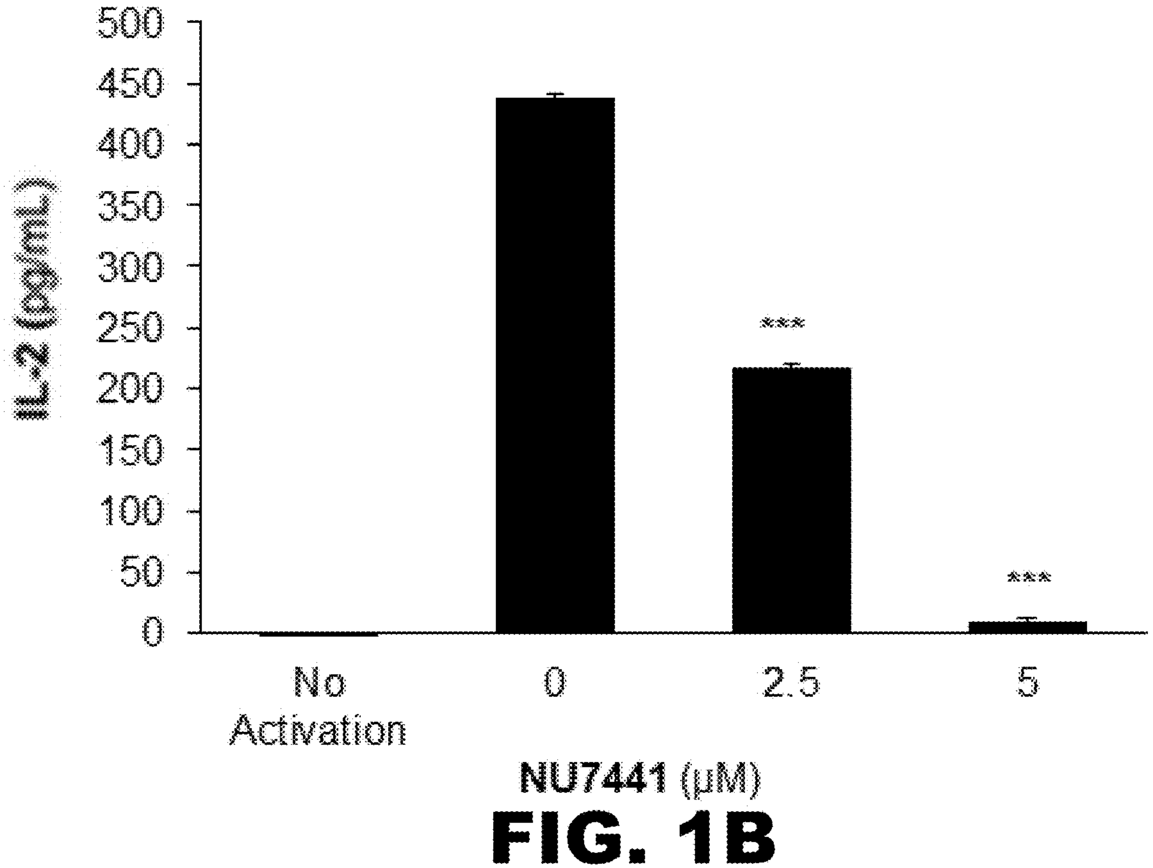
Figure 1C:
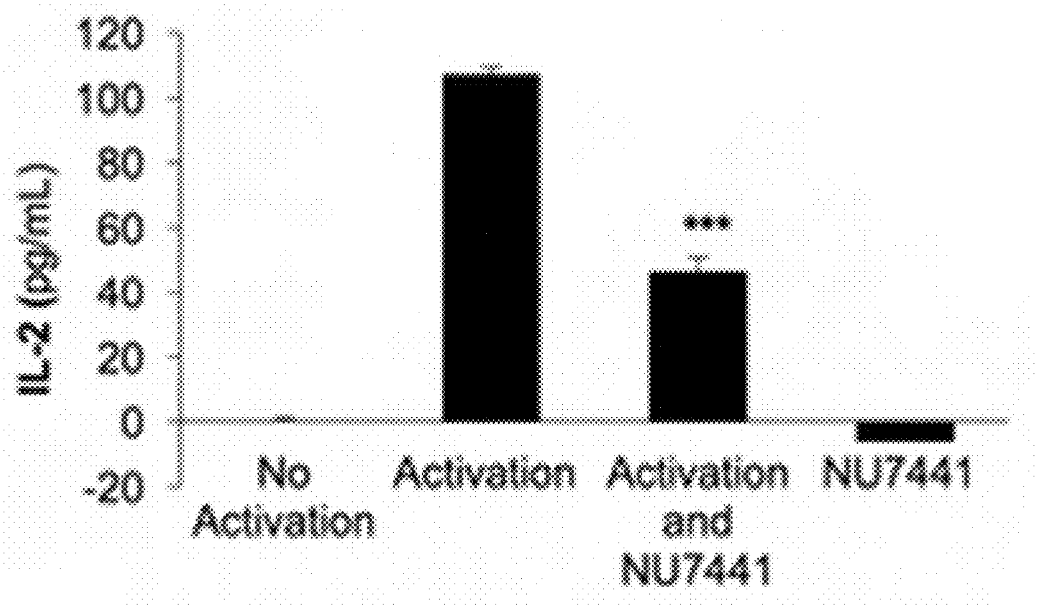
Figure 1D:
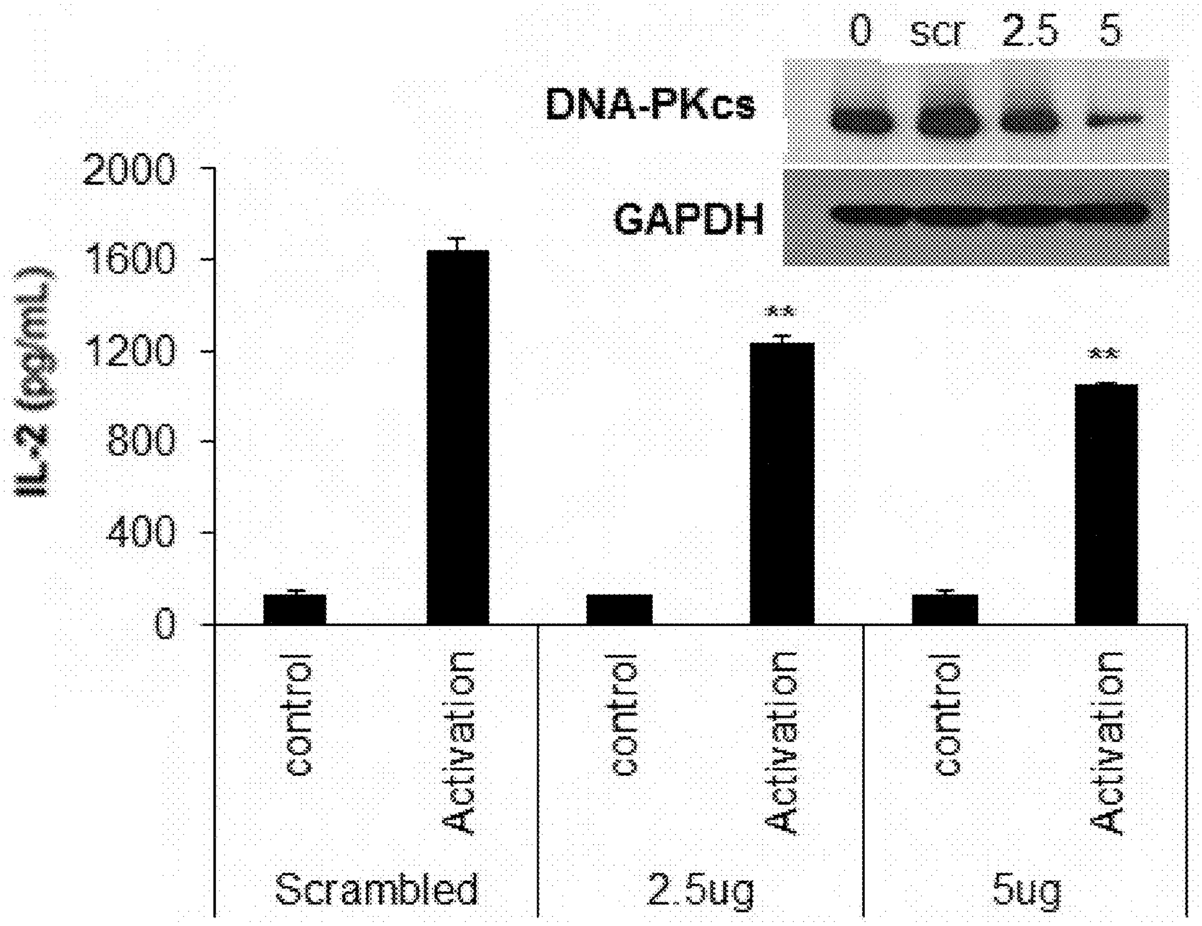

DNA-PKcs regulates IL-2 secretion in T cells: The immune cytokine IL-2 is a key element of the immune response affecting both the humoral and cell-mediated arms of the immune system. To determine if DNA-PKcs regulates T cell-mediated IL-2 production, the effect of the DNA-PKcs inhibitor NU7441 on IL-2 in Jurkat cells was evaluated. NU7441 is a potent and specific inhibitor of DNA-PKcs which does not interfere with ATR or ATM activation [24]. It was determined that NU7441 at varying concentrations did not alter the viability of Jurkat cells (FIG. 1A). Next, the production of IL-2 in Jurkat cells treated with NU7441 was monitored. In FIG. 1B, the expected spike in IL-2 levels following 24 hour stimulation with PMA+PHA was observed. In the presence of the inhibitor, the level of IL-2 was significantly decreased with 2.5 UM of NU7441 and further decreased with 5 μM (FIG. 1B). During an immune response, T cells are typically stimulated by activation of the T cell receptor (TCR). To determine if DNA-PKcs was acting in a TCR directed pathway, we repeated the IL-2 production assay after stimulating T cells with anti-CD28/CD3 dynabeads which activate the TCR. Cells were harvested 24 hours after stimulation and treatment with or without the NU7441 inhibitor. As seen with PMA+PHA activation, NU7441 significantly blocked IL-2 production stimulated by anti-CD28/CD3 dynabeads (FIG. 1C). To confirm that the effect of IL-2 secretion was specific to DNA-PKcs and not a side effect of the inhibitor, the expression of DNA-PKcs using short hairpin RNA plasmids (shRNA) was knocked down. The protein level of DNA-PKcs was reduced with shRNA indicating that the knock down of DNA-PKcs was successful (FIG. 1D). Loss of DNA-PKcs expression significantly inhibited secretion of IL-2 in T cells following activation with PMA+PHA confirming DNA-PKcs as a critical regulator of IL-2 production (FIG. 1D).

Figure 1E:
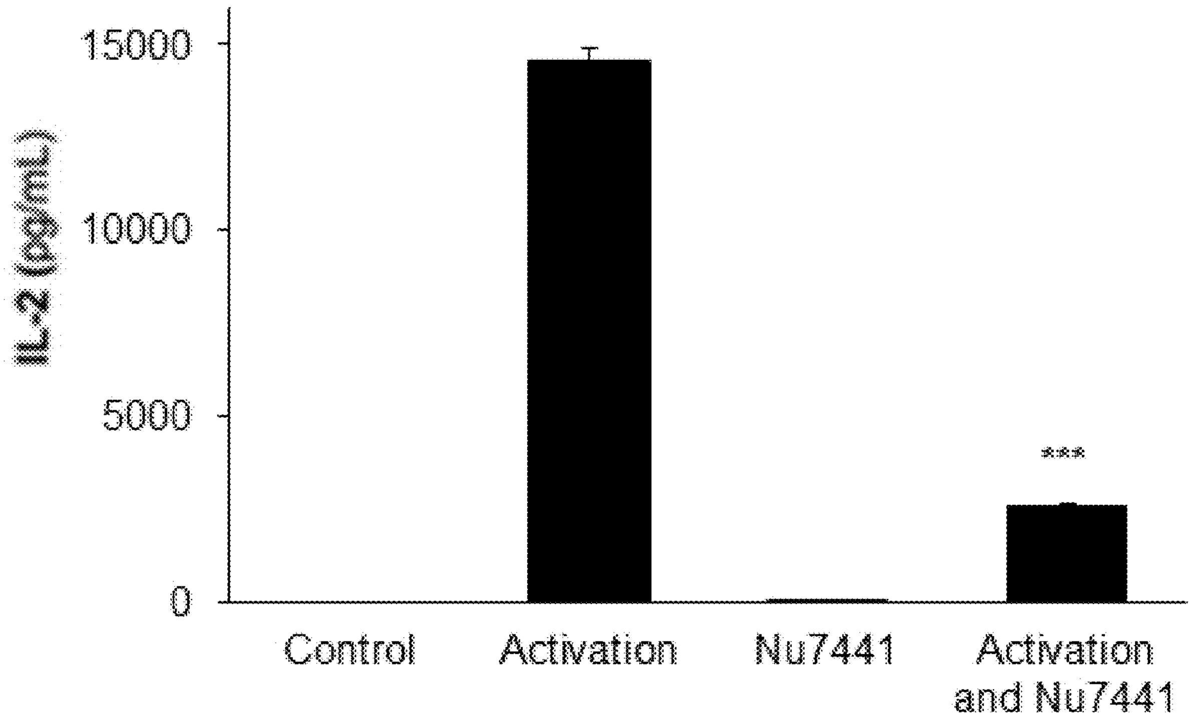
Figure 5:
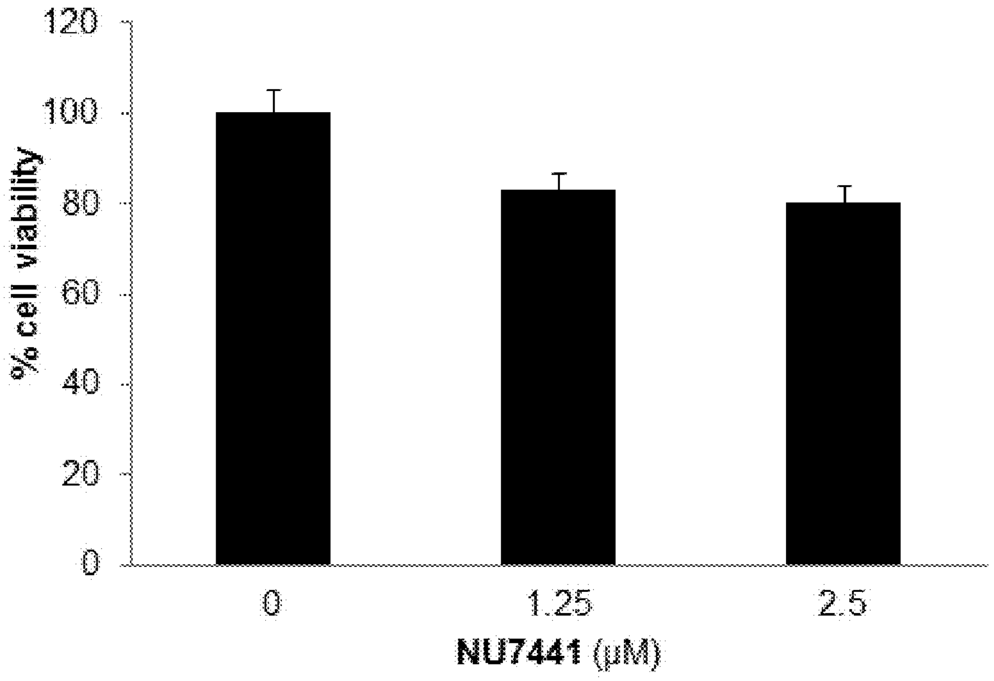
FIG. 5 depicts that treatment with NU7441 does not reduce cell viability in PBMC cells.

Next the effect of DNA-PKcs inhibition on IL-2 production in more clinically relevant human primary immune cells was examined. Therefore, DNA-PKcs activity in Peripheral Blood Mononuclear Cells, PMBC, was inhibited and the production of IL-2 was evaluated. Like Jurkat cells, NU7441 did not affect cellular viability but did significantly reduce the level of IL-2 produced following activation with PMA+PHA (FIG. 5 and FIG. 1E).

Figure 2A:
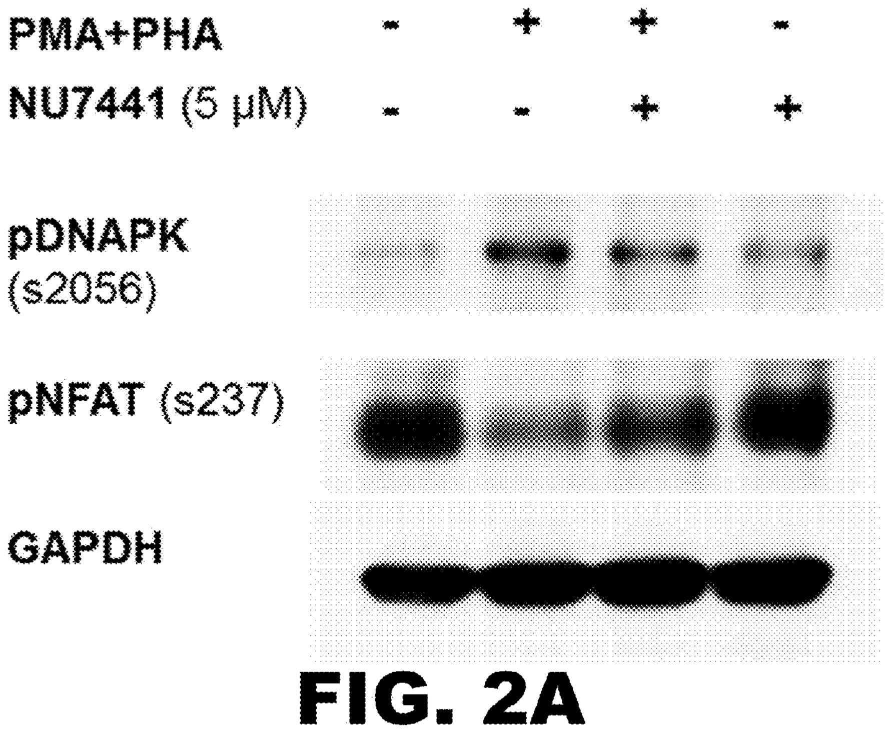
FIG. 2A and FIG. 2B depict inhibition of DNA-PKcs blocks translocation of NFAT to the nucleus.
Figure 2B:
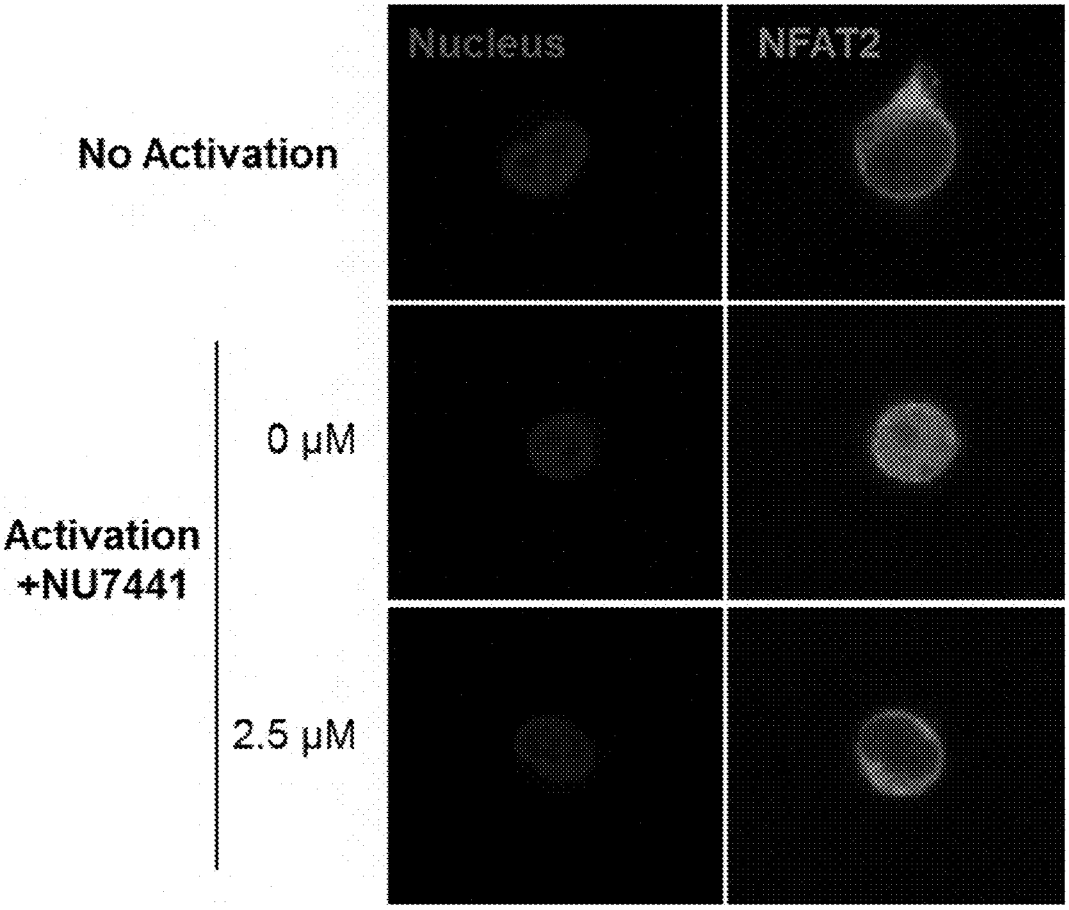

DNA-PKcs inhibition blocks nuclear localization of NFAT: IL-2 production is initiated by dephosphorylation and translocation of the transcription factor NFAT to the nucleus. Therefore, the effect of DNA-PKcs inhibition on NFAT in Jurkat cells by western blot and immunocytochemistry was examined. In FIG. 2A, it is shown that activation of Jurkat cells with PMA+PHA induced phosphorylation of DNA-PKcs at serine 2056, an activation site [25]. Additionally, NU7441 effectively inhibited DNA-PKcs phosphorylation confirming that NU7441 successfully inhibits DNA-PKcs activity. Without activation, NFAT was phosphorylated (s237) and resided in the cytoplasm in Jurkat cells (FIG. 2A and FIG. 2B). Upon activation, NFAT was dephosphorylated and translocated to the nucleus. However, in the presence of NU7441, NFAT remained phosphorylated and nuclear localization was prevented, further suggesting that DNA-PKcs is critical for proper T cell signaling (FIG. 0.2A and FIG. 2B).

Figure 3A:
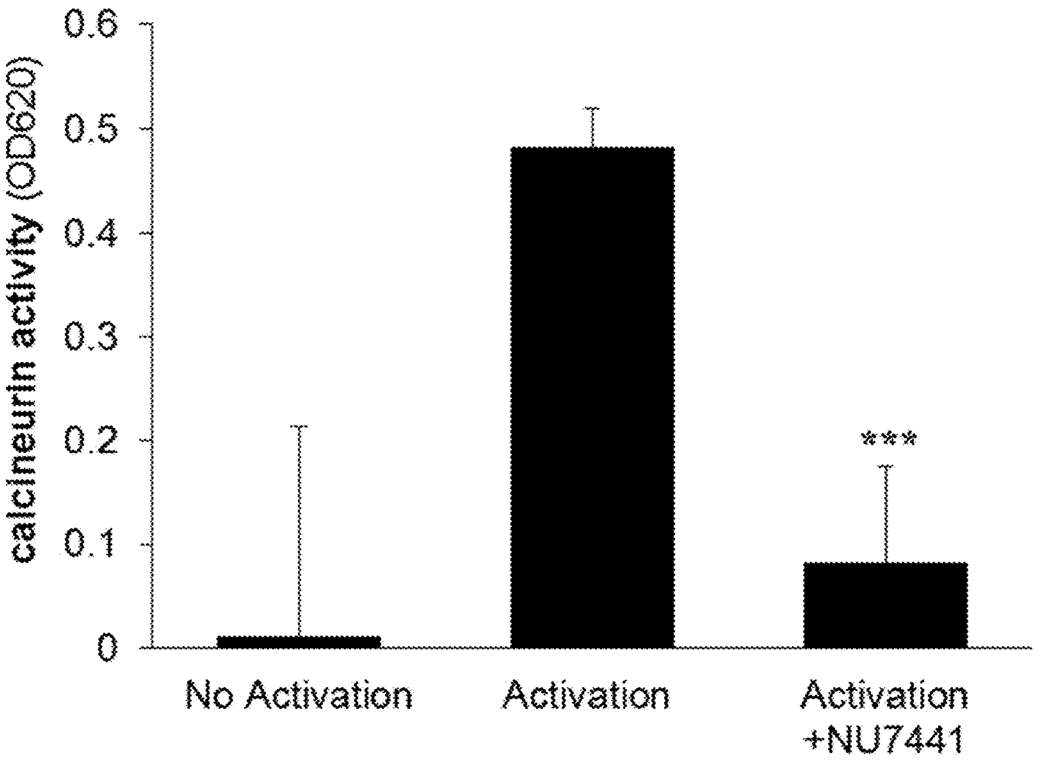
FIG. 3A, FIG. 3B, and FIG. 3C depict DNA-PKcs inhibition blocks calcineurin activity in T cells.
Figure 3B:
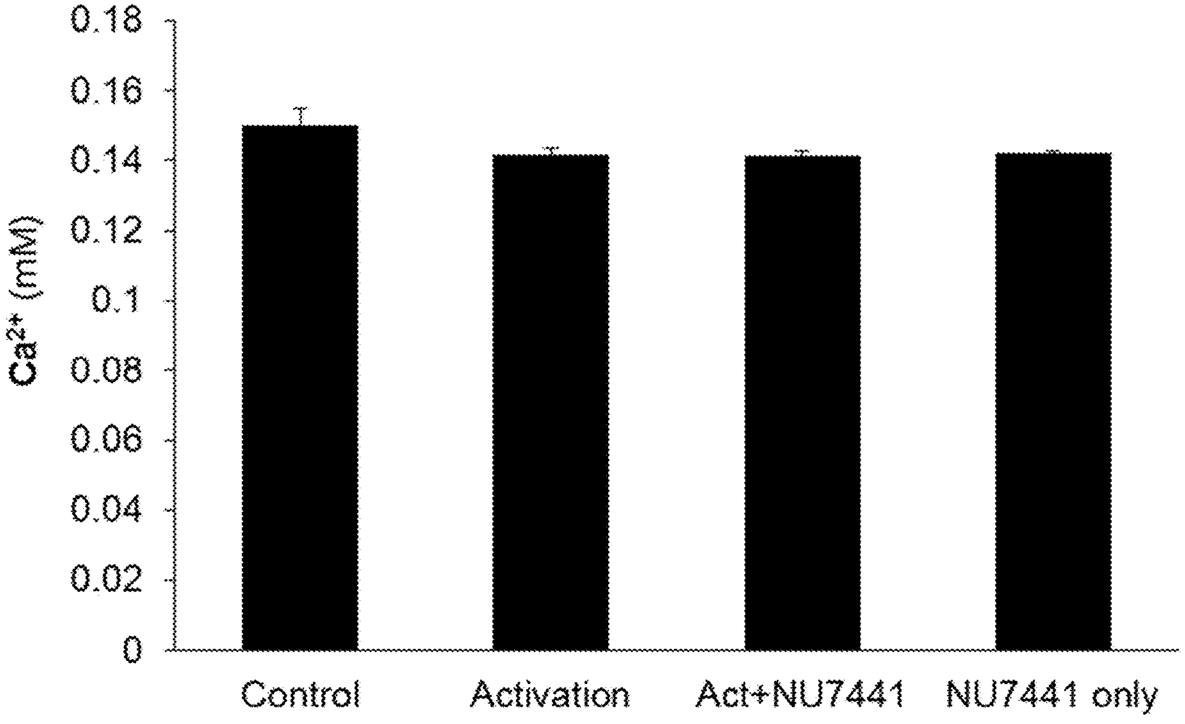

DNA-PKcs inhibition reduces calcineurin activity in T cells: As mentioned above, the regulation of NFAT is mediated via phosphorylation. During T cell activation, calcineurin, a calcium/calmodulin-dependent serine-threonine phosphatase, is activated and dephosphorylates NFAT allowing it to translocate to the nucleus to initiate transcription. Therefore, the effect of DNA-PKcs on calcineurin activity in Jurkat cells was evaluated. The phosphatase activity of calcineurin was greatly increased in the presence of PMA+PHA, however the activity was significantly inhibited with NU7441 treatment (FIG. 3A). Since the activity of calcineurin is regulated by the intracellular $Ca^{2+}$ ion concentration, the level of calcium ions was monitored. In the presence of NU7441 following activation, there was no change in the concentration of $Ca^{2+}$ ions (FIG. 3B) proving that DNA-PKcs does not regulate calcineurin activity by altering the influx of $Ca^{2+}$ but by a different unknown mechanism.

Figure 3C:
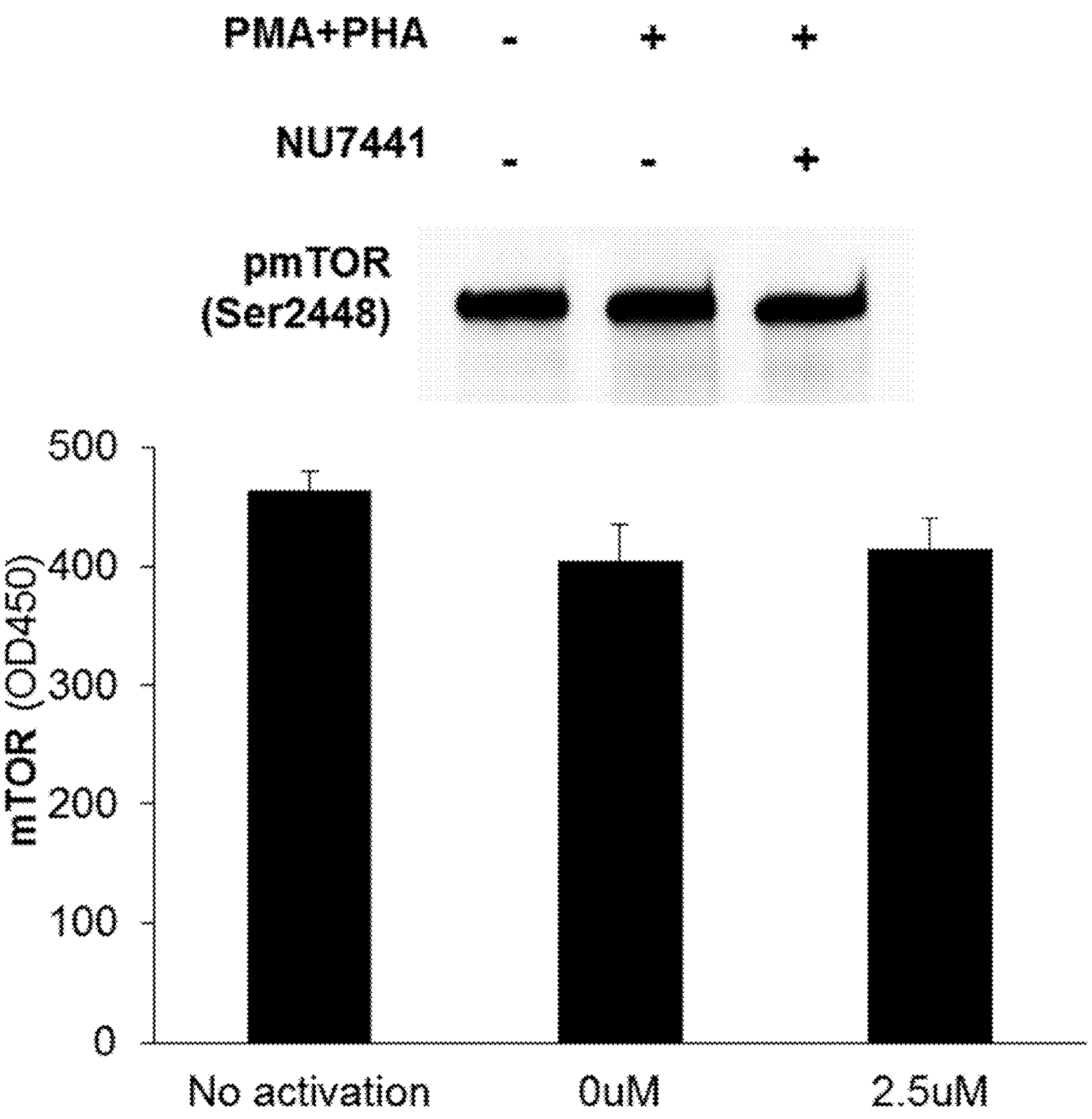

Mammalian target of rapamycin, mTOR, a member of the PI3K kinase family, is a second signaling pathway initiated following T cell activation [26]. Therefore, the effect of DNA-PKcs on the mTOR pathway was evaluated. Activated Jurkat cells with or without NU7441 treatment were subjected to an mTOR assay which detects the level of activated mTOR with an antibody specific to phosphorylated ser2448 was evaluated. Results from the assay along with western blot analysis of phosphorylated mTOR showed that loss of DNA-PKcs activity did not alter mTOR activation in T cells. (FIG. 3C). This further indicates a function for DNA-PKcs in T cells that is specific to the calcineurin signaling pathway.

Figure 4A:
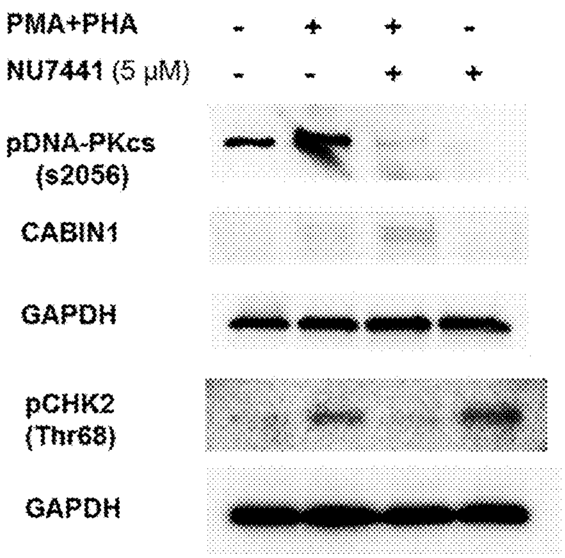
FIG. 4A and FIG. 4B depict inhibition of DNA-PKcs reduces phosphorylation of CHK2 and stabilizes the calcineurin inhibitor, Cabin1.
Figure 4B:
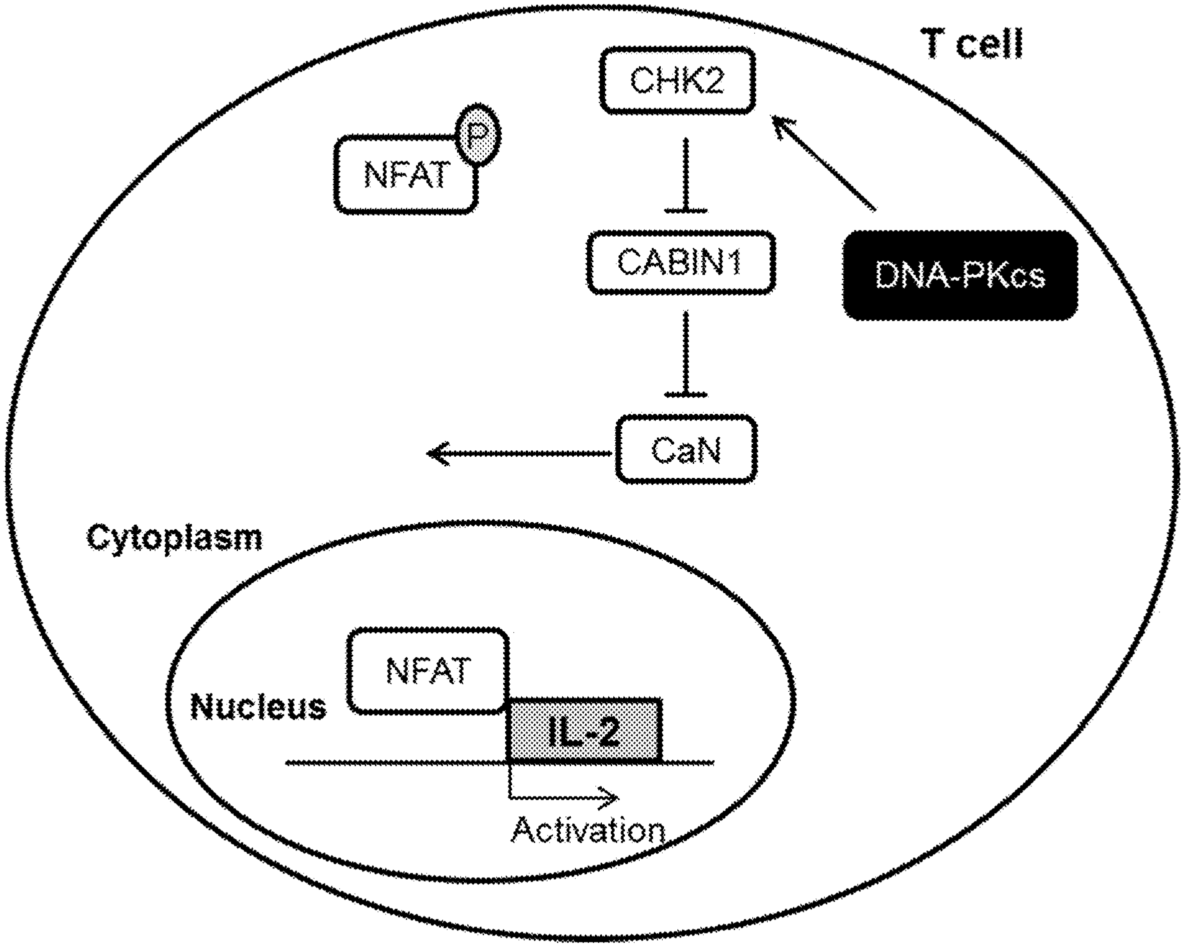

DNA-PKcs regulates expression of the calcineurin inhibitor Cabin1: The endogenous calcineurin inhibitor, Cabin1, binds calcineurin preventing the dephosphorylation of NFAT and transcription of immune cytokines including IL-2 [19, 20]. Cabin1 works in a similar fashion in the DNA damage repair pathway by binding p53 preventing its interaction with DNA [21, 22]. In this pathway, Cabin1 expression is controlled by checkpoint kinase CHK2. DNA damage signals the phosphorylation of CHK2 by DNA-PKcs at site T68 which stimulates CHK2 to hyper-phosphorylate Cabin1 targeting it for ubiquitination and degradation [23]. In this study, the relationship between DNA-PKcs, CHK2, and Cabin1 in the T cell signaling pathway was examined. We show that following activation of T cells, phosphorylation of DNA-PKcs (s2056) is increased along with an increase in CHK2 phosphorylation at Thr68 (FIG. 4A). Phosphorylation of both proteins was reduced with the NU744 inhibitor (FIG. 4A) indicating that DNA-PKcs is partly responsible for CHK2 activation in T cells. However, inhibition of DNA-PKcs and subsequently activation of CHK2 caused an increase in Cabin1 expression (FIG. 4A). This effect would result in a decrease in calcineurin activity and IL-2 production. These data highlight a novel mechanism by which DNA-PKcs regulates calcineurin signaling in T cells by its inhibitor Cabin1. A schematic of this mechanism is displayed in FIG. 4B.

Discussion

DNA-PKcs is a ubiquitously expressed enzyme with an increasing amount of functions defined in the literature. Not only is the enzyme critically important for NHEJ, but it has also been shown to phosphorylate a wide variety of substrates critical to cell growth, division, and homeostasis [10-14]. Mutations of DNA-PKcs in mammals present clinically with a SCID phenotype that is indistinguishable from other genetic causes of SCID [27]. Given its emerging function as a key regulator for numerous signaling transduction pathways, we hypothesized that DNA-PKcs not only affects the immune response through its role in V(D)J recombination but also by regulation of the calcineurin signaling pathway which stimulates the production of IL-2, a critical immune cell cytokine. Interestingly, DNA-PKcs has been previously reported to associate with proteins that bind to the antigen receptor response element in the IL-2 promoter region further suggesting a role for this protein in IL-2 regulation [28]. The IL-2 pathway has been extensively researched and has significant clinical importance particularly with respect to transplant, cancer, and cardiovascular biology. DNA-PKcs has not previously been linked to either mature T cell activation or the calcineurin signaling pathway. Using a Jurkat T cell model, a novel mechanism where DNA-PKcs regulates T cell-mediated signaling by altering the expression of the calcineurin inhibitor, Cabin1 was identified. The function of Cabin1 in T cell signaling has been well-characterized as a negative regulator of calcineurin activity [19, 20]. It was shown that through Cabin1, DNA-PKcs can exert control over the immune response. Like DNA-PKcs and CHK2, Cabin1 is involved in the DNA damage repair pathway. Cabin1 functions to inhibit the pathway by binding to p53 preventing its ability to bind DNA and promote transcription of DNA repair genes [21, 22]. Expression of Cabin1 is altered in response to DNA damage through activation of ATM and its target kinase, CHK2. Phosphorylation and activation of CHK2 result in degradation of Cabin1 freeing p53 to bind to DNA. DNA-PKcs has not been shown to effect Cabin1 expression, however; it does phosphorylate and activate CHK2 in response to DNA damage [23].

The results presented here underscore an additional role of DNA-PKcs in the immune system. Small molecule inhibition of DNA-PKcs is currently in Phase I clinical trials for cancer therapy with the idea being that chemoresistance can be usurped via disruption of a DNA double strand break repair pathway (Clinicaltrials.gov). Without being bound by theory, the results suggest that inhibition of this enzyme will likely have an immediate and profound effect on T-cell signaling in addition to its well-established role in V(D)J recombination. While the outcome of these clinical trials and the benefit of DNA-PKcs inhibitors as cancer therapy are still being evaluated, one could hypothesize the outcome. Loss of IL-2 expression due to these inhibitors could result in a reduced anti-oncogenic T cell response counteracting any positive effect from the inhibition of DNA damage repair. The effect of DNA-PKcs on IL-2 production must be considered when deciphering the outcome of these trials.

This work also highlights a novel use for DNA-PKcs inhibitors. Single drug small molecule inhibition of both cell mediated and humoral immunity is a goal of transplant pharmacology. Given this data, we feel that DNA-PKcs is a worthwhile target for immunosuppression in the transplant population as both an induction agent and possible maintenance therapy. Results from this study warrant investigation into the immunosuppression benefit of DNA-PKcs inhibition in transplant recipients.

REFERENCES

1. Burma S, Chen D J. Role of DNA-PK in the cellular response to DNA double-strand breaks. DNA Repair 2004; 3(8-9):909-18.
2. Davis A J, So S, Chen D J. Dynamics of the PI3K-like protein kinase members ATM and DNA-PKcs at DNA double strand breaks. Cell Cycle 2010; 9(13):2529-36.
3. Davis A J, Chen D J. DNA double strand break repair via non-homologous end-joining. Transl Cancer Res 2013; 2(3):130-143.
4. Taccioli G E, Amatucci A G, Beamish H J, Gell D, Xiang X H, Torres Arzayus M I, et al. Targeted disruption of the catalytic subunit of the DNA-PK gene in mice confers severe combined immunodeficiency and radiosensitivity. Immunity 1998; 9(3):355-66.
5. Jhappan C, Morse H C, 3rd, Fleischmann R D, Gottesman M M, Merlino G. DNA-PKcs: a T-cell tumour suppressor encoded at the mouse scid locus. Nat Genet 1997; 17(4): 483-6.
6. Gao Y, Chaudhuri J, Zhu C, Davidson L, Weaver D T, Alt F W. A Targeted DNA-PKcs-Null Mutation Reveals DNA-PK-Independent Functions for KU in V(D)J Recombination. Immunity 1998; 9(3):367-376
7. Alt F W, Yancopoulos G D, Blackwell T K, Wood C, Thomas E, Boss M, et al. Ordered rearrangement of immunoglobulin heavy chain variable region segments. Embo J 1984; 3(6):1209-19.
8. Born W, Yague J, Palmer E, Kappler J, Marrack P. Rearrangement of T-cell receptor beta-chain genes during T-cell development. Proc Natl Acad Sci USA 1985; 82(9):2925-9.
9. DiSanto J P, Dautry-Varsat A, Certain S, Fischer A, de Saint Basile G. Interleukin-2 (IL-2) receptor gamma chain mutations in X-linked severe combined immunodeficiency disease result in the loss of high-affinity IL-2 receptor binding. Eur J Immunol 1994; 24(2):475-9.
10. Minjgee M, Toulany M, Kehlbach R, Giehl K, Rodemann H P. K-RAS(V12) induces autocrine production of EGFR ligands and mediates radioresistance through EGFR-dependent Akt signaling and activation of DNA-PKcs. Int J Radiat Oncol Biol Phys 2011; 81(5):1506-14.
11. Burdine L J, Burdine M S, Moreland L, Fogel B, Orr L M, James J, et al. Proteomic Identification of DNA-PK Involvement within the RET Signaling Pathway. PLOS One 2015; 10(6).
12. Toulany M, Lee K J, Fattah K R, Lin Y F, Fehrenbacher B, Schaller M, et al. Akt promotes post-irradiation survival of human tumor cells through initiation, progression, and termination of DNA-PKcs-dependent DNA double-strand break repair. Mol Cancer Res 2012; 10(7): 945-57.

13. Dragoi A M, Fu X, Ivanov S, Zhang P, Sheng L, Wu D, et al. DNA-PKcs, but not TLR9, is required for activation of Akt by CpG-DNA. Embo J 2005; 24(4):779-89.
14. Wong R H, Chang I, Hudak C S, Hyun S, Kwan H Y, Sul H S. A role of DNA-PK for the metabolic gene regulation in response to insulin. Cell 2009; 136(6):1056-72.
15. Boyman O, Sprent J. The role of interleukin-2 during homeostasis and activation of the immune system. Nat Rev Immunol 2012; 12(3):180-90.
16. Hogan P G, Chen L, Nardone J, Rao A. Transcriptional regulation by calcium, calcineurin, and NFAT. Genes Dev 2003; 17(18):2205-32.
17. Liao W, Lin J X, Leonard W J. IL-2 family cytokines: new insights into the complex roles of IL-2 as a broad regulator of T helper cell differentiation. Curr Opin Immunol 2011; 23(5):598-604.
18. Malek T R, Castro I. Interleukin-2 receptor signaling: at the interface between tolerance and immunity. Immunity 2010; 33(2):153-65.
19. Sun L, Youn H D, Loh C, Stolow M, He W, Liu J O. Cabin 1, a negative regulator for calcineurin signaling in T lymphocytes. Immunity 1998; 8(6):703-11.
20. Esau C, Boes M, Youn H D, Tatterson L, Liu J O, Chen J. Deletion of calcineurin and myocyte enhancer factor 2 (MEF2) binding domain of Cabin1 results in enhanced cytokine gene expression in T cells. J Exp Med 2001; 194(10):1449-59.
21. Jang H, Choi S Y, Cho E J, Youn H D. Cabin1 restrains p53 activity on chromatin. Nat Struct Mol Biol 2009; 16(9):910-5.
22. Choi S Y, Jang H, Roe J S, Kim S T, Cho E J, Youn H D. Phosphorylation and ubiquitination-dependent degradation of CABIN1 releases p53 for transactivation upon genotoxic stress. Nucleic Acids Res 2013; 41(4):2180-90.
23. Li J, Stern D F. Regulation of CHK2 by DNA-dependent protein kinase. J Biol Chem 2005; 280(12):12041-50.
24. Leahy J J, Golding B T, Griffin R J, Hardcastle I R, Richardson C, Rigoreau L, et al. Identification of a highly potent and selective DNA-dependent protein kinase (DNA-PK) inhibitor (NU7441) by screening of chromenone libraries. Bioorganic and Medicinal Chemistry Letters 2004; 14(24):6083-7.
25. Chen B P, Chan D W, Kobayashi J, Burma S, Asaithamby A, Morotomi-Yano K, et al. Cell cycle dependence of DNA-dependent protein kinase phosphorylation in response to DNA double strand breaks. Journal of Biological Chemistry 2005; 280(15):14709-15.
26. Dennis P B, Fumagalli S, Thomas G. Target of rapamycin (TOR): balancing the opposing forces of protein synthesis and degradation. Current Opinion in Genetics and Development 1999; 9(1):49-54.
27. van der Burg M, van Dongen J J, van Gent D C. DNA-PKcs deficiency in human: long predicted, finally found. Curr Opin Allergy Clin Immunol 2009; 9(6):503-9.
28. Ting N S, Kao P N, Chan D W, Lintott L G, Lees-Miller S P. DNA-dependent protein kinase interacts with antigen receptor response element binding proteins NF90 and NF45. Journal of Biological Chemistry 1998; 273: 2136-2145.
29. Hein A L, Ouellette M M, Yan Y. Radiation-induced signaling pathways that promote cancer cell survival (review). International Journal of Oncology 2014; 45(5): 1813-9.
30. Golding S E, Morgan R N, Adams B R, Hawkins A J, Povirk L F, Valerie K. Pro-survival AKT and ERK signaling from EGFR and mutant EGFRvIII enhances DNA double-strand break repair in human glioma cells. Cancer Biol Ther 2009; 8(8):730-8.
31. Chen B P, Uematsu N, Kobayashi J, Lerenthal Y, Krempler A, Yajima H, et al. Ataxia telangiectasia mutated (ATM) is essential for DNA-PKcs phosphorylations at the Thr-2609 cluster upon DNA double strand break. Journal of Biological Chemistry 2007; 282(9): 6582-7.
32. Van Triest B, Damstrup L, Falkenius J, Budach V, Troost E, Samuels M, et al. A phase Ia/Ib trial of the DNA-dependent protein kinase inhibitor (DNA-PKi) M3814 in combination with radiotherapy in patients with advanced solid tumors. Journal of Clinical Oncology 2017; 35: e14048-e14048.

Example 2: Inhibition of DNA-PKcs as Immunosuppression Therapy for Transplant Patients Methods and Materials Materials: DNA-PK inhibitor, NU7441 was purchased from Selleckchem.com and used in vivo at 10 mg/kg diluted in DMSO and 40% PEG or in vitro at 5 μM. Tacrolimus (FK506) was ordered for Sigma Aldrich and used at a concentration of 1 mg/kg in vivo.

Mouse skin allograft: To confirm that DNA-PK inhibitors could function as an immunosuppressant in vivo, mouse skin allograft studies were performed. All studies were performed under an approved IACUC protocol. Ears from donor BALBc mice were removed and split into two removing all cartilaginous material. The ear skin was placed on an incision made to the back of a recipient C57Bl6 or DNA-PK knockout (NOD.CB17-Prkdc scid/J-20) mouse. The skin was sutured in 4 places using 6-0 nylon sutures. Wounds were wrapped in gauze and ban-daids and allowed to heal for 6 days before removing the bandage. Spleens were harvested from donor mice for splenocyte isolation. On Day 0 through Day 10 (the day of sacrifice) mice were injected (100 ul) daily with one of the following: saline, Tacrolimus (1 mg/kg), or NU7441 (1 mg/kg). Mice were monitored for rejection daily which was indicated by dark, black appearance. At the time of sacrifice, mice were euthanised according to IACUC guidelines and skin grafts removed and fixed in formalin for histology. Spleens and blood were also collected.

Evaluation of PD-1 and IL-2 expression: The effect of NU7441 on the expression of PD-1, a protein with immunosuppressant function, and IL-2 was examined in Jurkat cells following stimulation with PHA+PMA and treatment with the inhibitor NU7441. qPCR analysis was performed using primers specific for PD1 and IL-2 sequences.

qPCR on T cell markers: Naïve CD4+ T cells were isolated by standard methods from the spleens of Balbc mice. T cells were grown in culture and treated with cytokines specific for differentiate into Th1 and Th17 subtypes. Additionally, T cells were cultured with NU7441 and FK506. qPCR was performed looking at the following markers: Batf3, RORγt, IL17, IL22, TGFBeta, Lymphotoxin, T-Bet.

Results

Figure 6A:
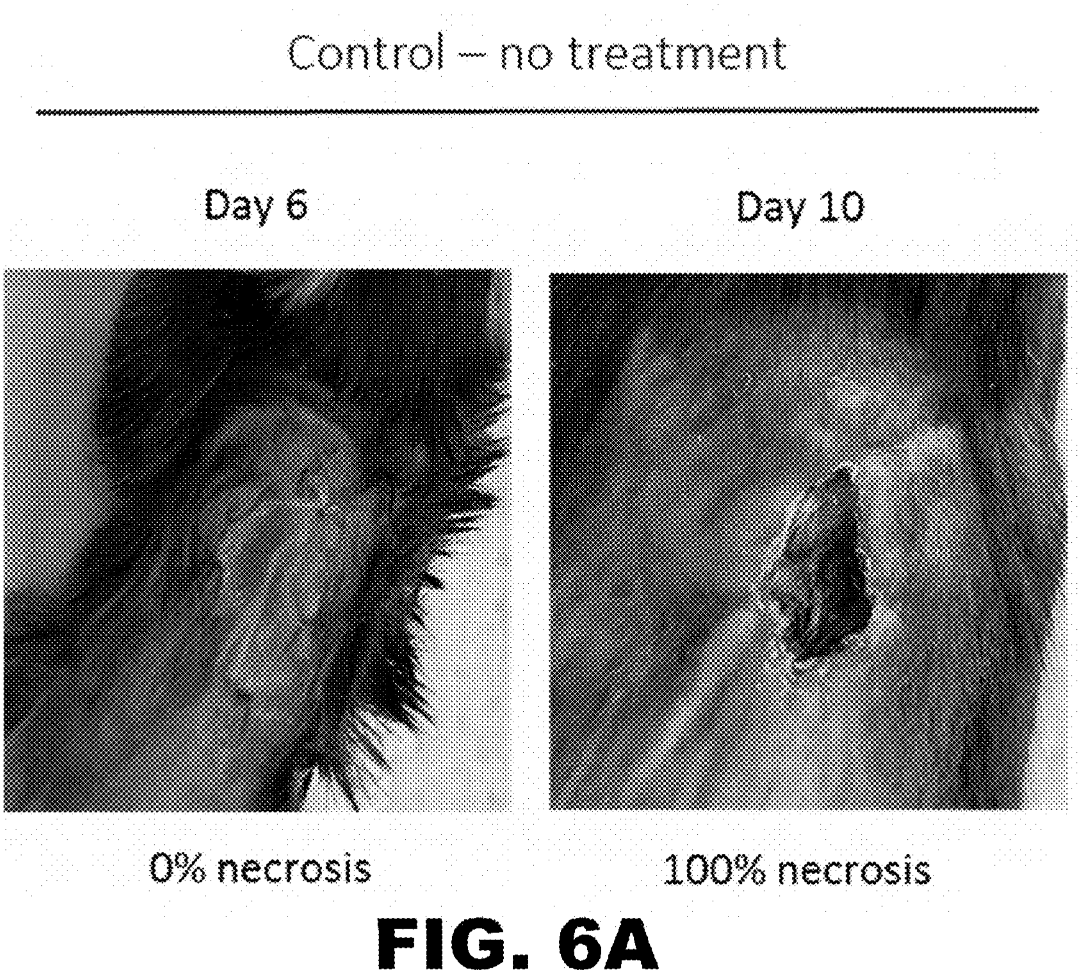
FIG. 6A, FIG. 6B, and FIG. 6C depict loss of DNA-PKcs activity reduces rejection in an allogeneic murine skin graft mode, (FIG. 6A) control and (FIG. 6B) DNA-PK inhibitor.
Figure 6B:
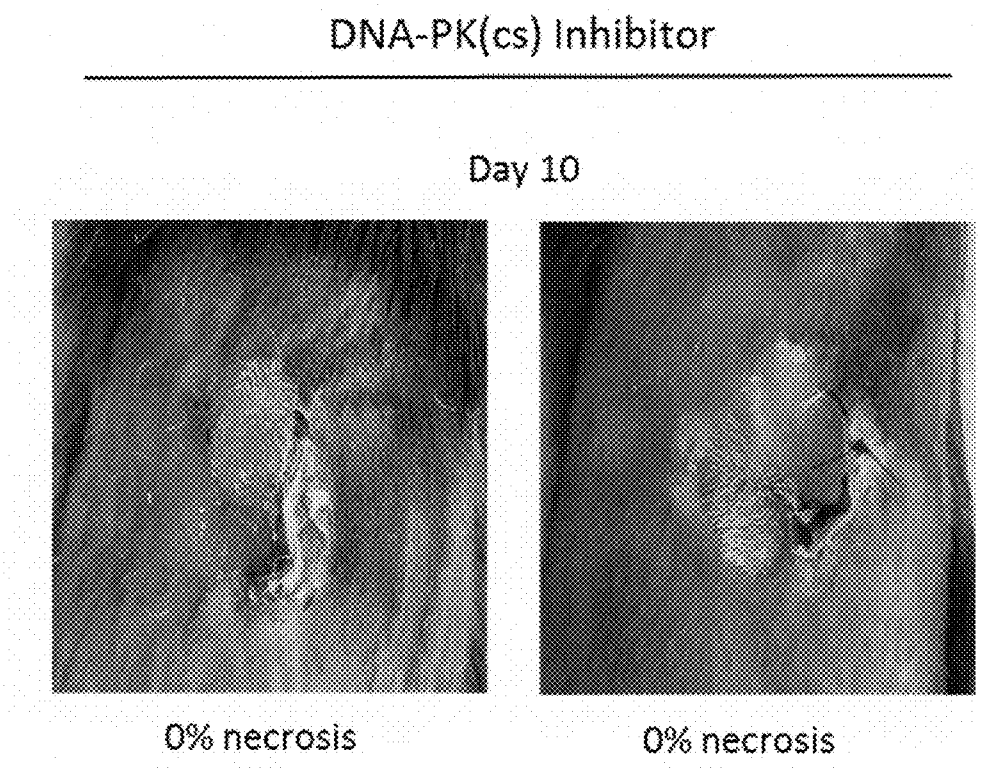
Figure 6C:
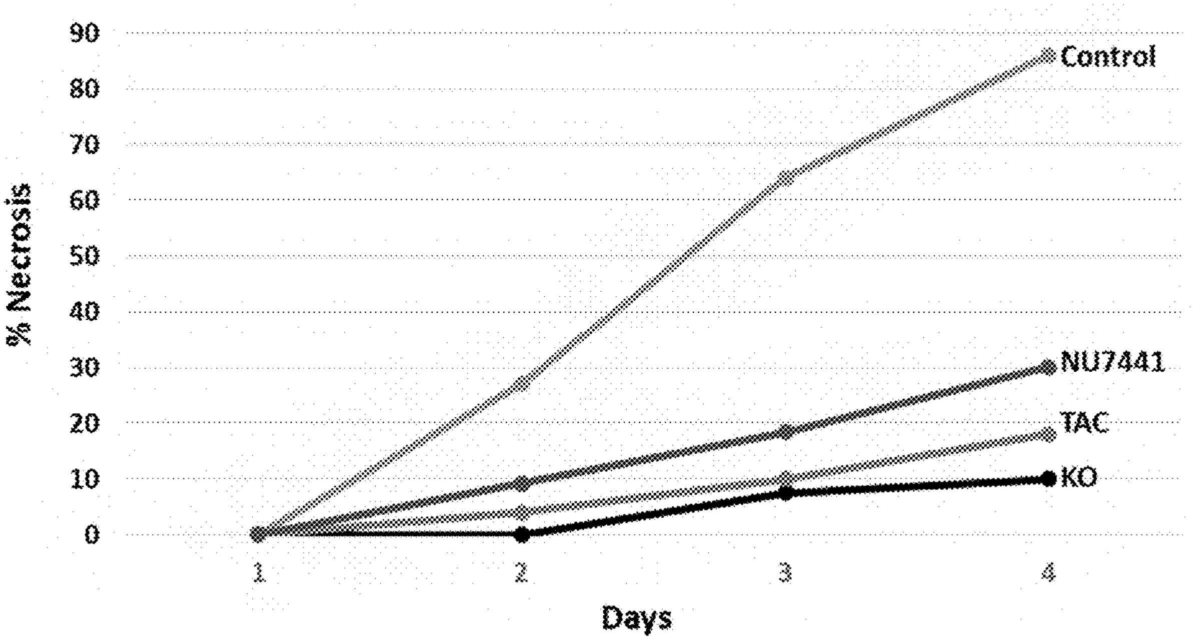
Figure 7A:
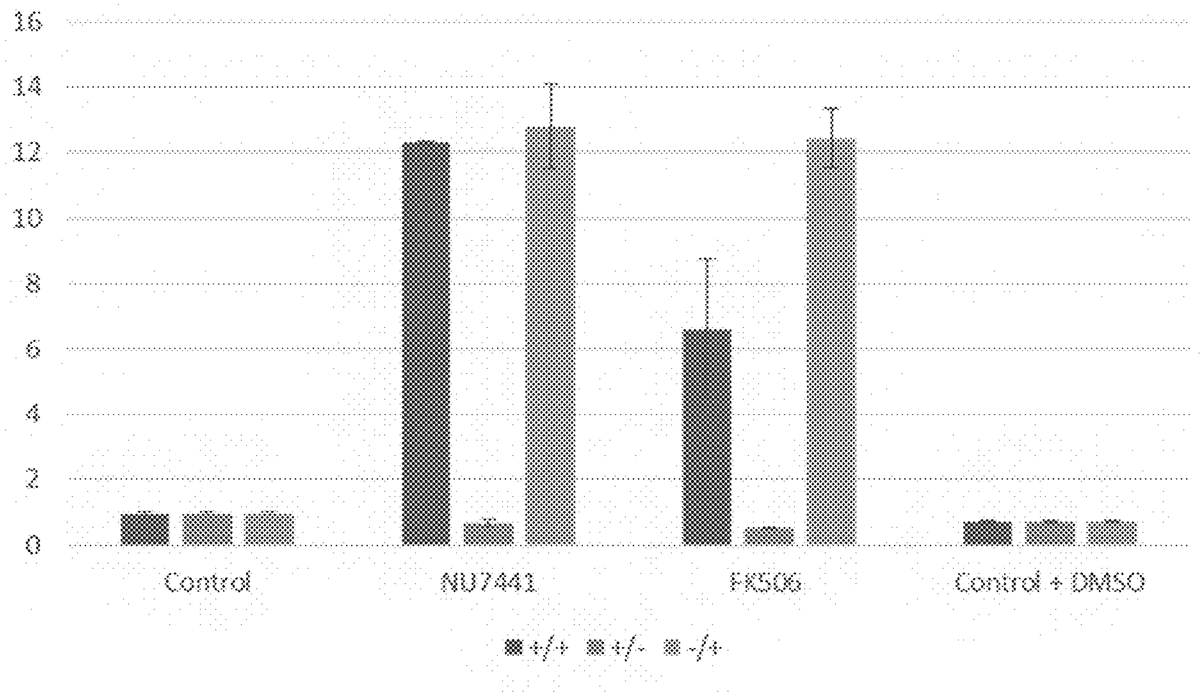
FIG. 7A and FIG. 7B depict DNA-PKcs inhibition does not affect PD-1 expression.
Figure 7B:
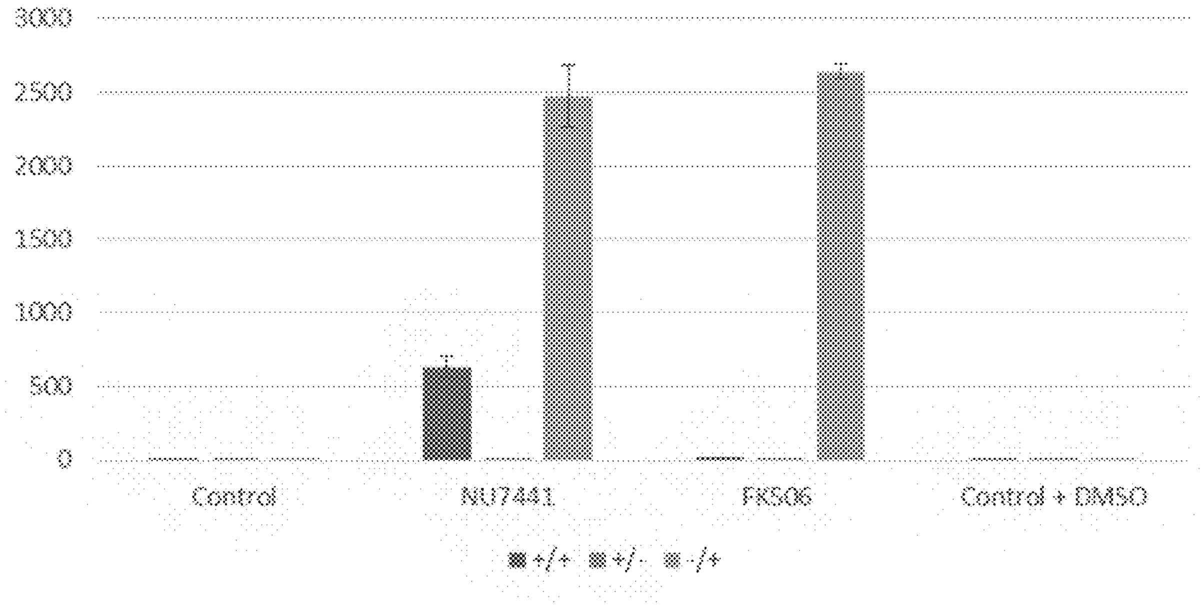
Figure 8A:
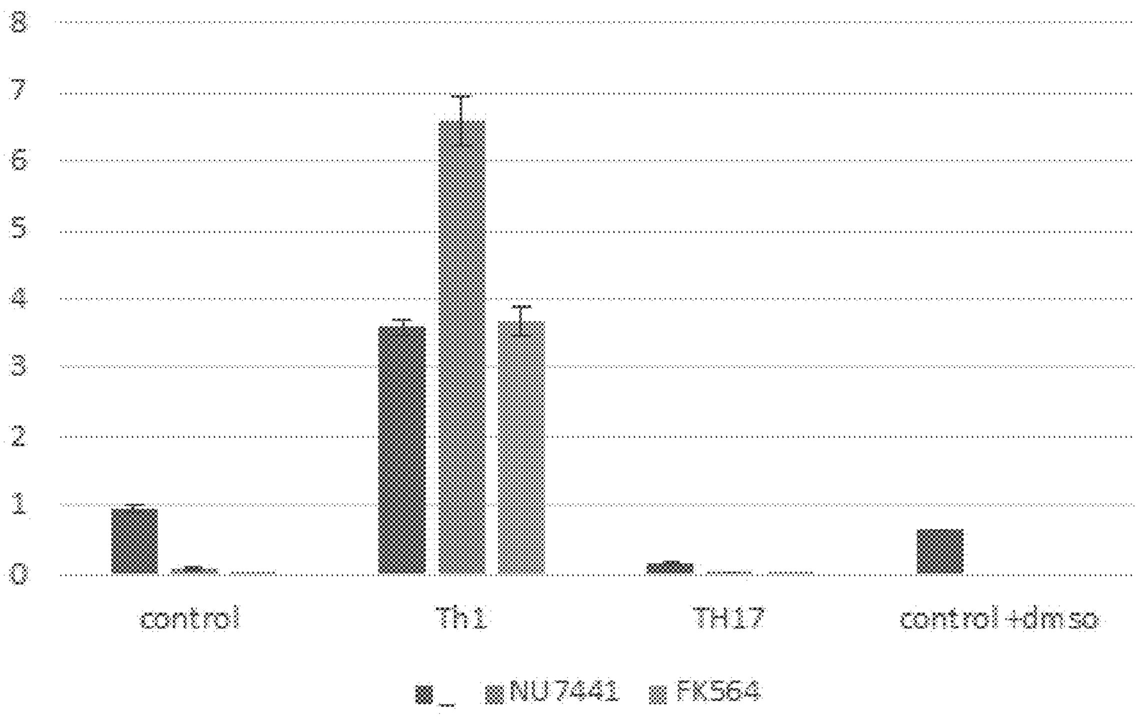
FIG. 8A and FIG. 8B depict DNA-PKcs inhibition promotes Th1 differentiation. qPCR analysis was performed on markers specific to Th1 cells following differentiation of naïve CD4+ T cells isolated from mouse spleens into the Th1 T cell subtype.
Figure 8B:
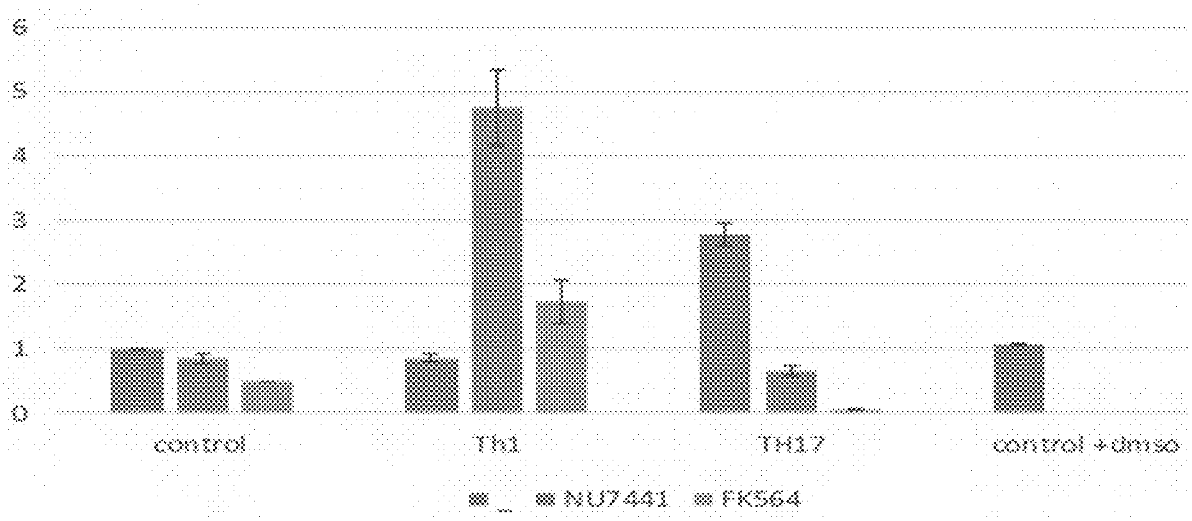
Figure 9A:
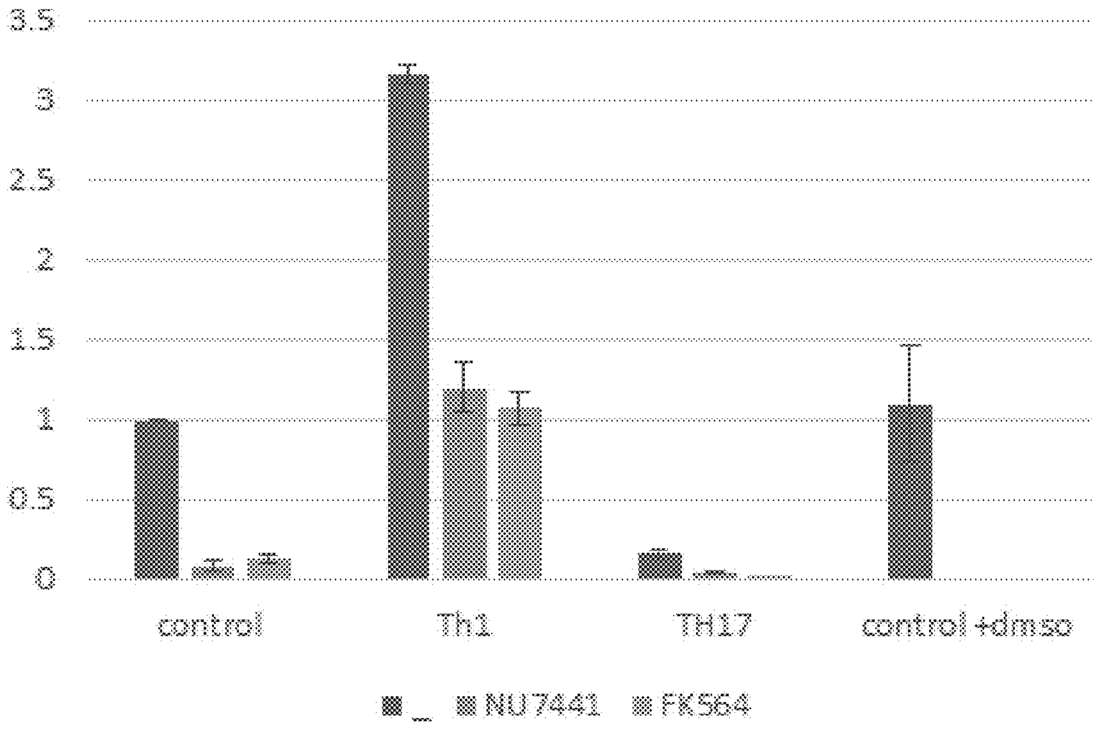
FIG. 9A, FIG. 9B, FIG. 9C, FIG. 9D, and FIG. 9E depict DNA-PKcs inhibition blocks Th17 differentiation. qPCR analysis was performed on markers specific to Th17 cells following differentiation of naïve CD4+ T cells isolated from mouse spleens into the Th17 T cell subtype.
Figure 9B:
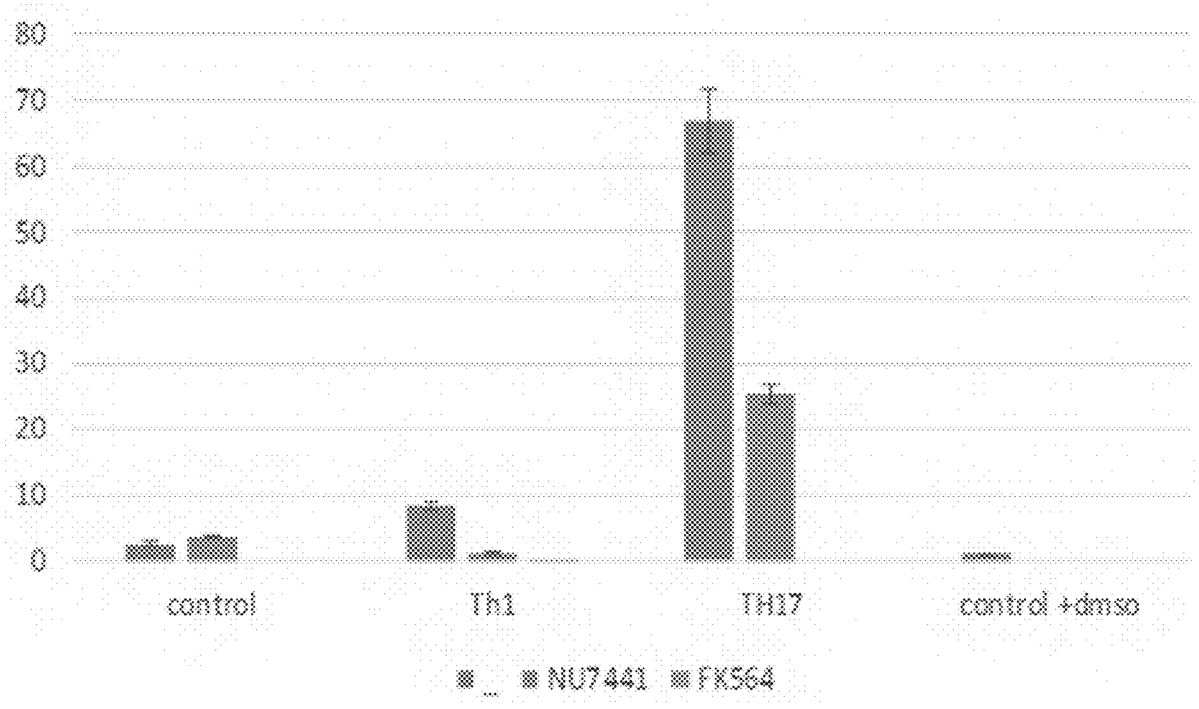
Figure 9C:
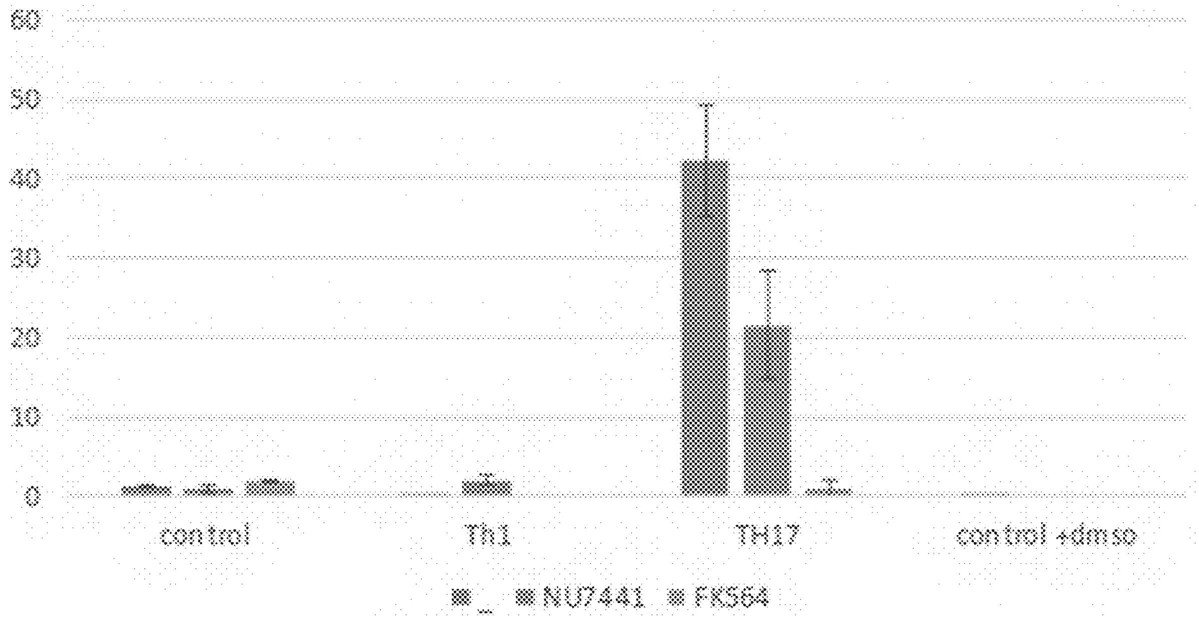
Figure 9D:
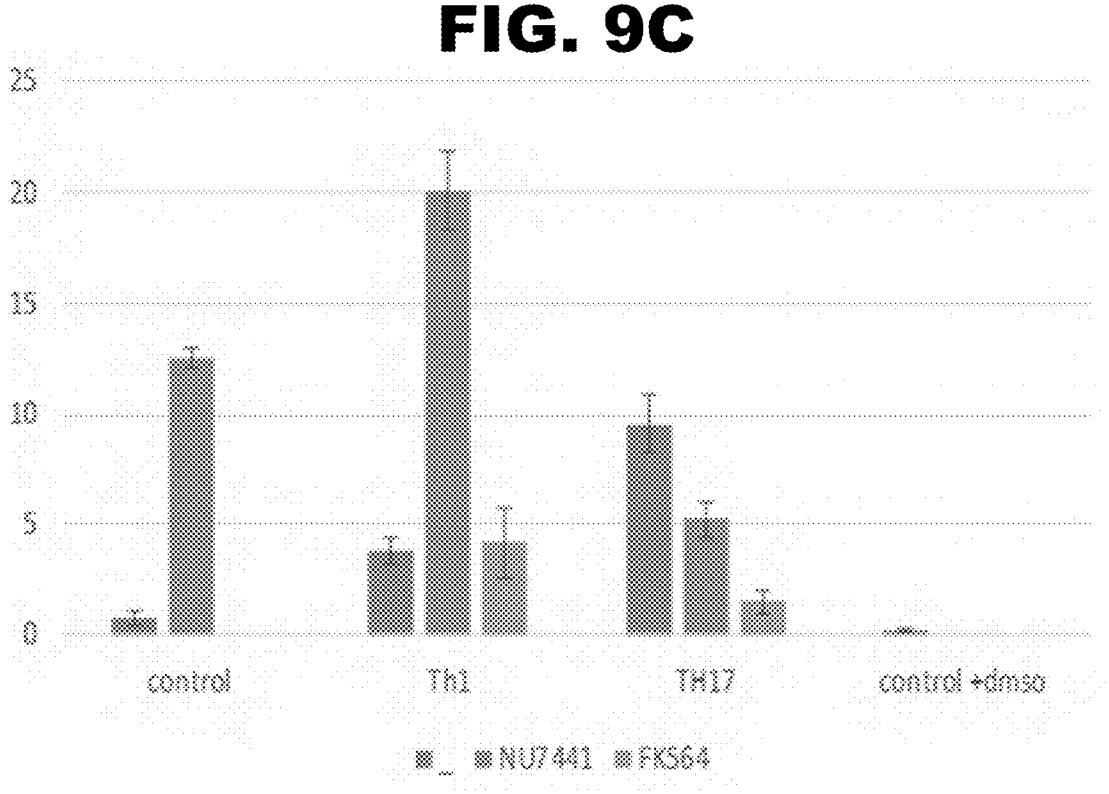
Figure 9E:
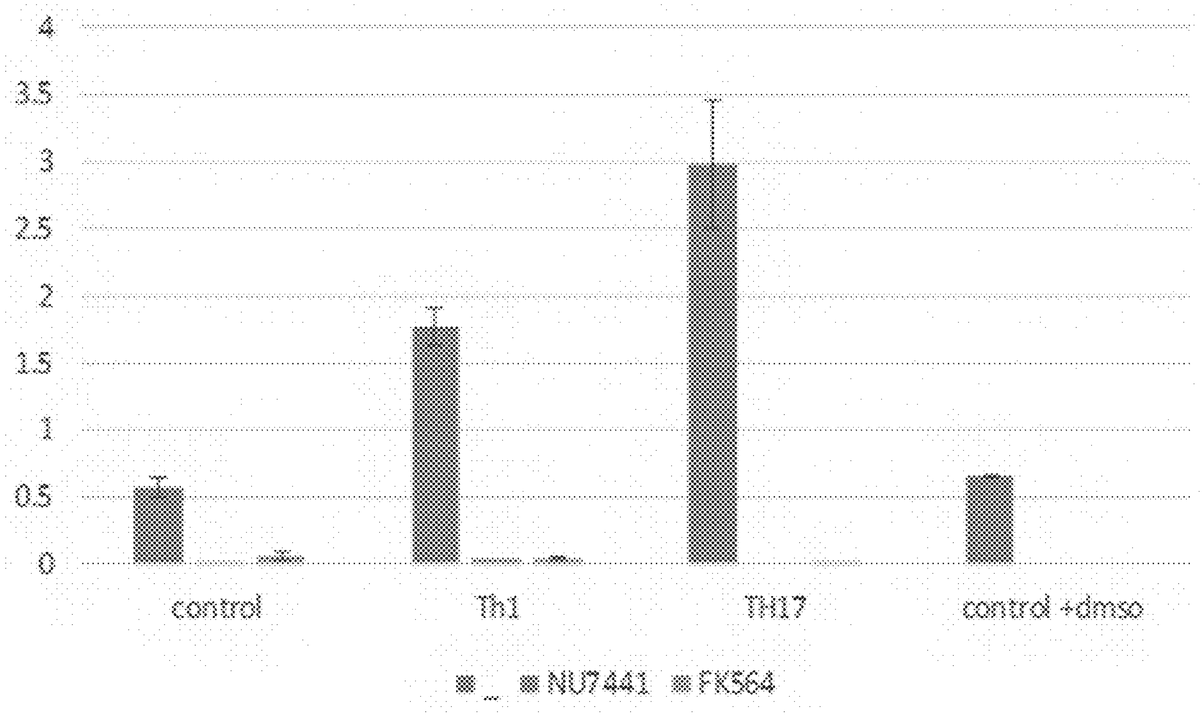

In the provided data we show that treatment with NU7441, a DNA-PK inhibitor, reduces rejection in a skin allograft mouse model compared to control groups treated only with saline. Visual examination of saline groups confirmed severe necrosis while NU7441 treatment groups had a majority with 0% necrosis (FIG. 6A). On Day 10 at the completion of the study, DNA-OK KO mice and NU7441 treated mice had a significant reduction in the level of necrosis with controls being around 80% on average and NU7441 around 30% and KO around 15-20% (FIG. 6B and FIG. 6C). This data confirms that DNA-PK inhibition is a legitimate means for immunosuppression following transplantation. Additionally, to understand better how DNA-PK is regulating the immune system, studies were performed to analyze the effect of DNA-PK inhibition on PD-1 expression given that PD-1 is a protein with immunosuppressant functions. Treatment with NU7441 did not alter the expression level of PD-1 although treatment with the calcineurin inhibitor FK506 did significantly reduce expression. IL-2 expression was reduced with both NU7441 and FK506 as expected given our prior studies showing NU7441 reduces Il-2 expression by inhibiting calcineurin activity (FIG. 7A and FIG. 7B). Next, studies were performed to analyze the effects of DNA-PK inhibition on T cell subtype differentiation since T cell subtypes often regulate immunity and disease outcome. qPCR analysis of specific subtype markers following treatment with different cytokines for differentiation along with NU7441 or FK506 indicated that NU7441 was promoting the expression of Th1 T cells while suppressing a Th17 environment. (FIG. 8A, FIG. 8B, FIG. 8C, FIG. 8D, and FIG. 9E). This information provides evidence that DNA-PK is a key regulator of the immune response and can alter the population of T cell subtype.

All cited references are herein expressly incorporated by reference in their entirety.

Whereas particular embodiments have been described above for purposes of illustration, it will be appreciated by those skilled in the art that numerous variations of the details may be made without departing from the disclosure as described in the appended claims.

What is claimed is:

1. A method of reducing graft rejection in a subject receiving an organ transplant, the method comprising administering to the subject a therapeutically effective amount of a composition comprising a DNA-PK inhibitor; wherein the subject is a human recipient of an allograft organ or organ tissue transplant, wherein the organ or the organ tissue is selected from the group consisting of kidney, liver, heart, lung, cornea, skin and a tissue thereof; wherein the administration of the DNA PK inhibitor reduces graft rejection in the subject compared to a subject not administered the DNA PK inhibitor; and wherein the DNA PK inhibitor is selected from (a) a small molecule inhibitor selected from VX-984, CC-115, NU7441, and NU-7026; and (b) a short-hairpin RNA (shRNA) comprising a sequence set forth in any one of SEQ ID NO: 6, 7, or 8.

2. The method of claim 1, wherein the reduced graft rejection is reduced chronic graft rejection.

3. The method of claim 1, wherein the reduced graft rejection is reduced acute graft rejection.

4. The method of claim 1, wherein the administration of the DNA-PK inhibitor suppresses T or B cell activity.

5. The method of claim 4, wherein the administration of the DNA-PK inhibitor suppresses T and B cell activity.

6. The method of claim 4, wherein the administration of the DNA-PK inhibitor suppresses T cell activity.

7. The method of claim 4, wherein the administration of the DNA-PK inhibitor suppresses B cell activity.

8. The method of claim 1, wherein the administration of the DNA-PK inhibitor suppresses IL-2 secretion in T-cells.

9. The method of claim 1, wherein the administration of the DNA PK inhibitor increases graft survival.

10. The method of claim 1, wherein the administration of the DNA PK inhibitor improves a transplantation outcome selected from decreased lymphocytic infiltration, vasculitis, infarction, ischemia, thrombosis, intimal thickening, glomerular atrophy, glomerular sclerosis, tubular atrophy, hyalinization, interstitial fibrosis, cortical fibrosis, serum creatinine levels, intimal proliferation, hypertrophy, cardiac vessel disease post-transplant, graft intimal hyperplasia, luminal occlusion, and bronchitis obliterans.

11. The method of claim 1, wherein the DNA-PK inhibitor composition is administered by parenteral administration.

12. The method of claim 11, wherein the parenteral administration is intravascular, intravenous, intra-arterial, subcutaneous, intramuscular, intraperitoneal, intraventricular, or intraepidermal administration.

13. A method of reducing an immune response in a subject receiving an organ or tissue transplant, the method comprising administering to the subject a therapeutically effective amount of a composition comprising a DNA-PK inhibitor, wherein the DNA-PK inhibitor improves the transplantation outcome; wherein the subject is a human recipient of an allograft organ or organ tissue transplant, wherein the organ or organ tissue is selected from the group consisting of kidney, liver, heart, lung, cornea tissue, skin, and a tissue thereof and wherein the DNA PK inhibitor is selected from (a) a small molecule inhibitor selected from VX-984, CC-115, NU7441, and NU-7026; and (b) a short-hairpin RNA (shRNA) comprising a sequence set forth in any one of SEQ ID NO: 6, 7, or 8.

14. The method of claim 1, wherein the therapeutically effective amount of the DNA-PK inhibitor is about 1 mg/kg.

15. The method of claim 1, wherein the organ tissue is skin tissue.

16. The method of claim 1, wherein the DNA-PK inhibitor is NU7441.

17. The method of claim 1, wherein the administration of the DNA-PK inhibitor reduces tissue or organ necrosis in the subject compared to a subject not administered the DNA PK inhibitor.

* * * * *

SEQUENCE LISTING

```
Sequence total quantity: 8
SEQ ID NO: 1            moltype = DNA  length = 29
FEATURE                 Location/Qualifiers
misc_feature            1..29
                        note = SYNTHESIZED
source                  1..29
                        mol_type = other DNA
                        organism = synthetic construct
SEQUENCE: 1
ctccagttct ggagcacctc gtggtgatg                                    29

SEQ ID NO: 2            moltype = DNA  length = 29
FEATURE                 Location/Qualifiers
misc_feature            1..29
                        note = SYNTHESIZED
source                  1..29
                        mol_type = other DNA
                        organism = synthetic construct
SEQUENCE: 2
ccgcaagcat aggtttcaac atcggagac                                    29

SEQ ID NO: 3            moltype = DNA  length = 29
FEATURE                 Location/Qualifiers
misc_feature            1..29
                        note = SYNTHESIZED
source                  1..29
                        mol_type = other DNA
                        organism = synthetic construct
SEQUENCE: 3
acagtgtggc atccagagta gcgaatact                                    29

SEQ ID NO: 4            moltype = DNA  length = 29
FEATURE                 Location/Qualifiers
misc_feature            1..29
                        note = SYNTHESIZED
source                  1..29
                        mol_type = other DNA
                        organism = synthetic construct
SEQUENCE: 4
tgaagcaaca tcagaatact atggaggac                                    29

SEQ ID NO: 5            moltype = DNA  length = 7085
FEATURE                 Location/Qualifiers
misc_feature            1..7085
                        note = SYNTHESIZED
source                  1..7085
                        mol_type = other DNA
                        organism = synthetic construct
SEQUENCE: 5
cgggaagggg cggtgcggga ggcggggtgt ggggcggtag tgtgggccct gttcctgccc  60
gcgcggtgtt ccgcattctg caagcctccg gagcgcacgt cggcagtcgg ctccctcgtt  120
gaccgaatca ccgacctctc tccccagggg gatccaccgg agcttaccat gaccgagtac  180
aagcccacgg tgcgcctcgc caccccgcgac gacgtcccca gggccgtacg caccctcgcc  240
gccgcgttcg ccgactaccc cgccacgcgc cacaccgtcg atccggaccg ccacatcgag  300
cgggtcaccg agctgcaaga actcttcctc acgcgcgtcg ggctcgacat cggcaaggtg  360
```

-continued

```
tgggtcgcgg acgacggcgc cgcggtggcg gtctggacca cgccggagag cgtcgaagcg  420
ggggcggtgt tcgccgagat cggcccgcgc atggccgagt tgagcggttc ccggctggcc  480
gcgcagcaac agatggaagg cctcctggcg ccgcaccggc ccaaggagcc cgcgtggttc  540
ctggccaccg tcggcgtctc gcccgaccac cagggcaagg gtctgggcag cgccgtcgtg  600
ctccccggag tggaggcggc cgagcgcgcc ggggtgcccg ccttcctgga gacctccgcg  660
ccccgcaacc tccccttcta cgagcggctc ggcttcaccg tcaccgccga cgtcgaggtg  720
cccgaaggac cgcgcacctg gtgcatgacc cgcaagcccg gtgcctgacg cccgccccac  780
gacccgcagc gcccgaccga aaggagcgca cgaccccatg catcggtacc tttaagacca  840
atgacttaca aggcagctgt agatcttagc cactttttaa aagaaaaggg gggactggaa  900
gggctaattc actcccaacg aagacaagat ctgctttttg cttgtactgg gtctctctgg  960
ttagaccaga tctgagcctg ggagctctct ggctaactag ggaacccact gcttaagcct  1020
caataaagct tgccttgagt gcttcaagta gtgtgtgccc gtctgttgtg tgactctggt  1080
aactagagat ccctcagacc cttttagtca gtgtggaaaa tctctagcag tagtagttca  1140
tgtcatctta ttattcagta tttataactt gcaaagaaat gaatatcaga gagtgagagg  1200
aacttgttta ttgcagctta taatggttac aaataaagca atagcatcac aaatttcaca  1260
aataaagcat ttttttcact gcattctagt tgtggtttgt ccaaactcat caatgtatct  1320
tatcatgtct ggctctagct atcccgcccc taactccgcc catcccgccc ctaactccgc  1380
ccagttccgc ccattctccg ccccatggct gactaatttt ttttatttat gcagaggccg  1440
aggccgcctc ggcctctgag ctattccaga agtagtgagg aggctttttt ggaggcctag  1500
ggacgtaccc aattcgccct atagtgagtc gtattacgcg cgctcactgg ccgtcgtttt  1560
acaacgtcgt gactgggaaa accctggcgt tacccaactt aatcgccttg cagcacatcc  1620
ccctttcgcc agctggcgta atagcgaaga ggcccgcacc gatcgccctt cccaacagtt  1680
gcgcagcctg aatggcgaat gggacgcgcc ctgtagcggc gcattaagcg cggcgggtgt  1740
ggtggttacg cgcagcgtga ccgctacact tgccagcgcc ctagcgcccg ctcctttcgc  1800
tttcttccct tcctttctcg ccacgttcgc cggctttccc cgtcaagctc taaatcgggg  1860
gctcccttta gggttccgat ttagtgcttt acggcacctc gaccccaaaa aacttgatta  1920
gggtgatggt tcacgtagtg ggccatcgcc ctgatagacg gtttttcgcc ctttgacgtt  1980
ggagtccacg ttctttaata gtggactctt gttccaaact ggaacaacac tcaaccctat  2040
ctcggtctat tcttttgatt tataagggat tttgccgatt tcggcctatt ggttaaaaaa  2100
tgagctgatt taacaaaaat ttaacgcgaa ttttaacaaa atattaacgc ttacaattta  2160
ggtggcactt ttcggggaaa tgtgcgcgga acccctattt gtttattttt ctaaatacat  2220
tcaaatatgt atccgctcat gagacaataa ccctgataaa tgcttcaata atattgaaaa  2280
aggaagagta tgagtattca acatttccgt gtcgccctta ttcccttttt tgcggcattt  2340
tgccttcctg tttttgctca cccagaaacg ctggtgaaag taaaagatgc tgaagatcag  2400
ttgggtgcac gagtgggtta catcgaactg gatctcaaca gcggtaagat ccttgagagt  2460
tttcgccccg aagaacgttt tccaatgatg agcactttta aagttctgct atgtggcgcg  2520
gtattatccc gtattgacgc cgggcaagag caactcggtc gccgcataca ctattctcag  2580
aatgacttgg ttgagtactc accagtcaca gaaaagcatc ttacggatgg catgacagta  2640
agagaattat gcagtgctgc cataaccatg agtgataaca ctgcggccaa cttacttctg  2700
acaacgatcg gaggaccgaa ggagctaacc gcttttttgc acaacatggg ggatcatgta  2760
actcgccttg atcgttggga accggagctg aatgaagcca taccaaacga cgagcgtgac  2820
accacgatgc ctgtagcaat ggcaacaacg ttgcgcaaac tattaactgg cgaactactt  2880
actctagctt cccggcaaca attaatagac tggatggagg cggataaagt tgcaggacca  2940
cttctgcgct cggcccttcc ggctggctgg tttattgctg ataaatctgg agccggtgag  3000
cgtgggtctc gcggtatcat tgcagcactg gggccagatg gtaagccctc ccgtatcgta  3060
gttatctaca cgacggggag tcaggcaact atggatgaac gaaatagaca gatcgctgag  3120
ataggtgcct cactgattaa gcattggtaa ctgtcagacc aagtttactc atatatactt  3180
tagattgatt taaaacttca tttttaattt aaaaggatct aggtgaagat cctttttgat  3240
aatctcatga ccaaaatccc ttaacgtgag ttttcgttcc actgagcgtc agaccccgta  3300
gaaaagatca aaggatcttc ttgagatcct ttttttctgc gcgtaatctg ctgcttgcaa  3360
acaaaaaaac caccgctacc agcggtggtt tgtttgccgg atcaagagct accaactctt  3420
tttccgaagg taactggctt cagcagagcg cagataccaa atactgttct tctagtgtag  3480
ccgtagttag gccaccactt caagaactct gtagcaccgc ctacatacct cgctctgcta  3540
atcctgttac cagtggctgc tgccagtggc gataagtcgt gtcttaccgg gttggactca  3600
agacgatagt taccggataa ggcgcagcgg tcgggctgaa cggggggttc gtgcacacag  3660
cccagcttgg agcgaacgac ctacaccgaa ctgagatacc tacagcgtga gctatgagaa  3720
agcgccacgc ttcccgaagg gagaaaggcg gacaggtatc cggtaagcgg cagggtcgga  3780
acaggagagc gcacgaggga gcttccaggg ggaaacgcct ggtatcttta tagtcctgtc  3840
gggtttcgcc acctctgact tgagcgtcga tttttgtgat gctcgtcagg ggggcggagc  3900
ctatggaaaa acgccagcaa cgcggccttt ttacggttcc tggccttttg ctggcctttt  3960
gctcacatgt tctttcctgc gttatcccct gattctgtgg ataaccgtat taccgccttt  4020
gagtgagctg ataccgctcg ccgcagccga acgaccgagc gcagcgagtc agtgagcgag  4080
gaagcggaag agcgcccaat acgcaaaccg cctctccccg cgcgttggcc gattcattaa  4140
tgcagctggc acgacaggtt tcccgactgg aaagcgggca gtgagcgcaa cgcaattaat  4200
gtgagttagc tcactcatta ggcaccccag gctttacact ttatgcttcc ggctcgtatg  4260
ttgtgtggaa ttgtgagcgg ataacaattt cacacaggaa acagctatga ccatgattac  4320
gccaagcgcg caattaaccc tcactaaagg gaacaaaagc tggagctgca agcttaatgt  4380
agtcttatgc aatactcttg tagtcttgca acatggtaac gatgagttag caacatgcct  4440
tacaaggaga gaaaaagcac cgtgcatgcc gattggtgga agtaaggtgg tacgatcgtg  4500
ccttattagg aaggcaacag acgggtctga catggattgg acgaaccact gaattgccgc  4560
attgcagaga tattgtattt aagtgcctag ctcgatacat aaacgggtct ctctggttag  4620
accagatctg agcctgggag ctctctggct aactagggaa cccactgctt aagcctcaat  4680
aaagcttgcc ttgagtgctt caagtagtgt gtgcccgtct gttgtgtgac tctggtaact  4740
agagatccct cagacccttt tagtcagtgt ggaaaatctc tagcagtggc gcccgaacag  4800
ggacttgaaa gcgaaaggga aaccagagga gctctctcga cgcaggactc ggcttgctga  4860
agcgcgcacg gcaagaggcg aggggcggcg actggtgagt acgccaaaaa ttttgactag  4920
cggaggctag aaggagagag atgggtgcga gagcgtcagt attaagcggg ggagaattag  4980
atcgcgatgg gaaaaaattc ggttaaggcc agggggaaag aaaaaatata aattaaaaca  5040
tatagtatgg gcaagcaggg agctagaacg attcgcagtt aatcctggcc tgttagaaac  5100
```

-continued

```
atcagaaggc tgtagacaaa tactgggaca gctacaacca tcccttcaga caggatcaga  5160
agaacttaga tcattatata atacagtagc aaccctctat tgtgtgcatc aaaggataga  5220
gataaaagac accaaggaag ctttagacaa gatagaggaa gagcaaaaca aaagtaagac  5280
caccgcacag caagcggccg ctgatcttca gacctggagg aggagatatg agggacaatt  5340
ggagaagtga attatataaa tataaagtag taaaaattga accattagga gtagcaccca  5400
ccaaggcaaa gagaagagtg gtgcagagag aaaaaagagc agtgggaata ggagctttgt  5460
tccttgggtt cttgggagca gcaggaagca ctatgggcgc agcgtcaatg acgctgacgg  5520
tacaggccag acaattattg tctggtatag tgcagcagca gaacaatttg ctgagggcta  5580
ttgaggcgca acagcatctg ttgcaactca cagtctgggg catcaagcag ctccaggcaa  5640
gaatcctggc tgtggaaaga tacctaaagg atcaacagct cctggggatt tggggttgct  5700
ctggaaaact catttgcacc actgctgtgc cttggaatgc tagttggagt aataaatctc  5760
tggaacagat ttggaatcac acgacctgga tggagtggga cagagaaatt aacaattaca  5820
caagcttaat acactcctta attgaagaat cgcaaaacca gcaagaaaag aatgaacaag  5880
aattattgga attagataaa tgggcaagtt tgtggaattg gtttaacata acaaattggc  5940
tgtggtatat aaaattattc ataatgatag taggaggctt ggtaggttta agaatagttt  6000
ttgctgtact ttctatagtg aatagagtta ggcagggata ttcaccatta tcgtttcaga  6060
cccacctccc aaccccgagg ggacccgaca ggcccgaagg aatagaagaa gaaggtggag  6120
agagagacag agacagatcc attcgattag tgaacggatc tcgacggtat cgatcacgag  6180
actagcctcg agcggccgcc cccttcaccg agggcctatt tcccatgatt ccttcatatt  6240
tgcatatacg atacaaggct gttagagaga taattggaat taatttgact gtaaacacaa  6300
agatattagt acaaaatacg tgacgtagaa agtaataatt tcttgggtag tttgcagttt  6360
taaaattatg ttttaaaatg gactatcata tgcttaccgt aacttgaaag tatttcgatt  6420
tcttggcttt atatatcttg tggaaaggac gaaacaccgg tcctaaggtt aagtcgccct  6480
cgctcgagcg agggcgactt aaccttaggt tttgaattcc tcgacctcga gacaaatggc  6540
agtattcatc cacaatttta aaagaaaagg ggggattggg gggtacagtg caggggaaag  6600
aatagtagac ataatagcaa cagacataca aactaaagaa ttacaaaaac aaattacaaa  6660
aattcaaaat tttcgggttt attacaggga cagcagagat ccactttggc cgcggctcga  6720
gggggttggg gttgcgcctt ttccaaggca gccctgggtt tgcgcaggga cgcggctgct  6780
ctgggcgtgg ttccgggaaa cgcagcggcg ccgaccctgg gtctcgcaca ttcttcacgt  6840
ccgttcgcag cgtcacccgg atcttcgccg ctacccttgt gggccccccg gcgacgcttc  6900
ctgctccgcc cctaagtcgg gaaggttcct tgcggttcgc ggcgtgccgg acgtgacaaa  6960
cggaagccgc acgtctcact agtaccctcg cagacggaca gcgccaggga gcaatggcag  7020
cgcgccgacc gcgatgggct gtggccaata gcggctgctc agcagggcgc gccgagagca  7080
gcggc                                                               7085

SEQ ID NO: 6           moltype = DNA  length = 21
FEATURE                Location/Qualifiers
misc_feature           1..21
                       note = SYNTHESIZED
source                 1..21
                       mol_type = other DNA
                       organism = synthetic construct
SEQUENCE: 6
gcgacatatt atggaagaat t                                           21

SEQ ID NO: 7           moltype = DNA  length = 21
FEATURE                Location/Qualifiers
misc_feature           1..21
                       note = SYNTHESIZED
source                 1..21
                       mol_type = other DNA
                       organism = synthetic construct
SEQUENCE: 7
ccacccaaca acaatatgat t                                           21

SEQ ID NO: 8           moltype = DNA  length = 21
FEATURE                Location/Qualifiers
misc_feature           1..21
                       note = SYNTHESIZED
source                 1..21
                       mol_type = other DNA
                       organism = synthetic construct
SEQUENCE: 8
gccatacaaa tgtggaatta a                                           21
```